US009848625B2

(12) United States Patent
Astrup et al.

(10) Patent No.: US 9,848,625 B2
(45) Date of Patent: Dec. 26, 2017

(54) COMPOSITIONS AND METHODS FOR INCREASING THE SUPPRESSION OF HUNGER AND REDUCING THE DIGESTIBILITY OF NON-FAT ENERGY SATIETY

(71) Applicant: University of Copenhagen, Copenhagen K (DK)

(72) Inventors: Arne Astrup, Klampenborg (DK); Inge Tetens, Ballerup (DK); Mette Kristensen, Copenhagen S (DK)

(73) Assignee: University of Copenhagen, Copenhagen (DK)

( * ) Notice: Subject to any disclaimer, the term of this patent is extended or adjusted under 35 U.S.C. 154(b) by 0 days.

(21) Appl. No.: 14/720,095

(22) Filed: May 22, 2015

(65) Prior Publication Data

US 2015/0320817 A1 Nov. 12, 2015

Related U.S. Application Data

(63) Continuation of application No. 12/676,583, filed as application No. PCT/DK2008/000321 on Sep. 12, 2008, now Pat. No. 9,066,536.

(60) Provisional application No. 60/971,798, filed on Sep. 12, 2007, provisional application No. 60/971,827, filed on Sep. 12, 2007.

(30) Foreign Application Priority Data

Sep. 12, 2007 (DK) .................................. 2007 01319
Sep. 12, 2007 (DK) .................................. 2007 01320

(51) Int. Cl.
*A23L 1/29* (2006.01)
*A61K 33/06* (2006.01)
*A61K 45/06* (2006.01)
*A61K 31/337* (2006.01)
*A61K 31/536* (2006.01)
*A61K 36/55* (2006.01)
*A23K 10/30* (2016.01)
*A23L 33/00* (2016.01)
*A23L 33/105* (2016.01)
*A23L 33/22* (2016.01)

(52) U.S. Cl.
CPC .............. *A23L 1/293* (2013.01); *A23K 10/30* (2016.05); *A23L 33/105* (2016.08); *A23L 33/22* (2016.08); *A23L 33/30* (2016.08); *A23L 33/40* (2016.08); *A61K 31/337* (2013.01); *A61K 31/536* (2013.01); *A61K 33/06* (2013.01); *A61K 36/55* (2013.01); *A61K 45/06* (2013.01); *A23V 2002/00* (2013.01)

(58) Field of Classification Search
CPC ...................................................... A61K 36/00
See application file for complete search history.

(56) References Cited

U.S. PATENT DOCUMENTS

| 4,598,089 A | 7/1986 | Hadvary et al. |
| 4,857,326 A | 8/1989 | Stitt |
| 5,110,592 A | 5/1992 | Stitt |
| 5,612,074 A | 3/1997 | Leach |
| 5,643,874 A | 7/1997 | Bremer et al. |
| 6,475,530 B1 | 11/2002 | Kuhrts |
| 6,579,544 B1 | 6/2003 | Rosenberg et al. |
| 7,977,319 B1* | 7/2011 | Levine ................... A21D 2/183 426/590 |
| 2002/0091110 A1 | 7/2002 | Bruckner et al. |
| 2002/0197275 A1 | 12/2002 | Sunvold et al. |
| 2004/0170738 A1 | 9/2004 | Wolt et al. |
| 2004/0171694 A1 | 9/2004 | Van Laere et al. |
| 2004/0241134 A1 | 12/2004 | Adams |
| 2006/0067986 A1* | 3/2006 | Zemel .................... A23C 21/02 424/439 |

(Continued)

FOREIGN PATENT DOCUMENTS

| CA | 501186D | 2/1955 |
| CN | 1426702 | 7/2003 |

(Continued)

OTHER PUBLICATIONS

Mazza et al, Functional properties of flax seed mucilage. Journal of Food Science (1989), 54(5), 1302-5.*
Rodriguez et al., "Effect of inclusion level of linseed on the nutrient utilisation of diets for growing broiler chickens," British Poultry Science, 2001, vol. 42, pp. 368-375.
Sandstrom et al., "A high oat-bran intake does not impair zinc absorption in humans when added to a low-fiber animal protein-based diet," The Journal of Nutrition, 2000, vol. 130, pp. 594-599.
Scheideler, Dr. Sheila E. et al., "Use of Enzymes in Poultry Rations Containing Flaxseed", Dept. of Animal Sci., University of Nebraska, 1996, pp. 97-100.

(Continued)

*Primary Examiner* — Qiuwen Mi
(74) *Attorney, Agent, or Firm* — Posternak Blankstein & Lund LLP

(57) ABSTRACT

The present invention relates to methods for increasing the suppression of hunger and/or increasing the reduction of prospective consumption and/or increasing the reduction of appetite and/or increasing the feeling of satiety and/or reducing non-fat energy uptake in the gastrointestinal tract of a mammal in order to prevent a positive non-fat energy balance, weight gain, overweight and obesity, and to induce a negative non-fat energy balance and weight loss in subjects who wish to reduce their body weight. In particular, feed, food and/or beverages and dietary supplements of the present invention comprises mucilage such as flax seed mucilage and/or one or more active compounds of mucilage useful for increasing the suppression of hunger and/or increasing the reduction of prospective consumption and/or increasing the reduction of appetite and/or increasing the feeling of satiety and/or reducing the digestibility of non-fat energy in the gastrointestinal tract of a mammal.

25 Claims, 13 Drawing Sheets

(56) References Cited

U.S. PATENT DOCUMENTS

| | | |
|---|---|---|
| 2007/0036874 A1 | 2/2007 | Zhong |
| 2007/0078179 A1* | 4/2007 | Edgar ................ A61K 31/192 514/449 |
| 2008/0299646 A1* | 12/2008 | Chang .................. C12P 19/04 435/274 |

FOREIGN PATENT DOCUMENTS

| | | |
|---|---|---|
| DE | 706631 | 5/1941 |
| DE | 3739700 | 6/1989 |
| EP | 1491099 | 12/2004 |
| EP | 1679009 | 7/2006 |
| GB | 535321 | 4/1941 |
| GB | 2008408 | 6/1979 |
| JP | 1197440 | 8/1989 |
| JP | 2001-275613 | 10/2001 |
| JP | 2002047194 | 2/2002 |
| JP | 2002536988 | 11/2002 |
| JP | 2003-528642 | 9/2003 |
| JP | 2004083428 | 3/2004 |
| WO | WO 93/16707 | 9/1993 |
| WO | WO 9316707 A1 * | 9/1993 |
| WO | WO 93/21774 | 11/1993 |
| WO | WO 97/35594 | 10/1997 |
| WO | WO 99/33450 | 7/1999 |
| WO | WO 00/19842 | 4/2000 |
| WO | WO 00/49896 | 8/2000 |
| WO | WO 01/74179 | 10/2001 |
| WO | WO01/87075 A1 | 11/2001 |
| WO | WO 2005/107777 | 11/2005 |

OTHER PUBLICATIONS

Schulstad et al., Bread and Health, article on homepage at http://www.schulstad.dk/external/schulstad/webbuilder.nsf/0/01ad66cda6f1e879c1256d . . . , dated Dec. 15, 2003.
Sosulski et al., "Composition and Physiological Properties of Several Sources of Dietary Fiber," Journal of Food Science, 1982, vol. 47, pp. 1472-1477.
Velasquez, et al., "Dietary flaxseed meal reduces proteinuria and ameliorates nephropathy in an animal model of type II diabetes mellitus," Kidney International, 2003, vol. 64, pp. 2100-2107.
Wisker et al., "Contribution of barley fiber to the metabloizable energy of human diets," Nutrition Research, 1992, vol. 12, pp. 1315-1323.
Wolever et al., Effect of Dietary Fiber and Foods on Carbohydrate Metabolism, CRC handbook of Dietary Fiber in Human Nutrition 3rd Edition, CRC Press, 2001, pp. 321-360.
FAO/WHO, FAO/WHO/UNU, "Energy and Protein Requirements," Technical Report Series 724, World Health Organization, Geneva, 1985, http://www.fao.org/docrep/003/AA040E/AA040E00.HTM.
International Search Report dated Aug. 5, 2005, cited in International Application No. PCT/DK2005/000314.
International Search Report and Written Opinion dated Dec. 19, 2008 for PCT/DK2008/000321.
Brahe et al., "Specific gut microbiota features and metabolic markers in postmenopausal women with obesity," Nutrition and Diabetes, 2015, vol. 5. pp. 1-7.
Dulloo et al. "Energy balance and body weight regulation," Human Nutrition, Eleventh Edition, pp. 96-97 (2005).
Gibbons et al. "Comparison of Postprandial Profiles of Ghrelin, Active GLP-1, and Total PYY to Meals Varying in Fat and Carbohydrate and Their Association With Hunger and the Phases of Satiety," J Clin Endocrinol Metab. vol. 98, No. 5, pp. E847-E855 (2013).
Hlebowicz et al. "Effect of commercials breakfast fibre cereals compared with corn flakes on postprandial blood glucose, gastric emptying and satiety in healthy subjects: a randomized blinded crossover trial," Nutrition Journal, vol. 6, No. 22, pp. 1-7 (2007).

Guerin et al. "Changes in intragastric meal distribution are better predictors of gastric emptying rate in conscious pigs than are meal viscosity or dietary fibre concentration," British Journal of Nutrition, vol. 85, pp. 343-350 (2001).
Ibrugger, Sabine et al., "Flaxseed dietary fiber supplements for suppression of appetite and food intake," Appetite, 2012, vol. 58, pp. 490-495.
Kristensen, M. et al., "Whole Flaxseeds but not sunflower seed in rye bread reduce apparent digestibility of fat in healthy volunteers," European Journal of Clinical Nutrition, 2008, vol. 62, pp. 961-967.
Kristensen, M. et al., "Flaxseed dietary fibers suppress postprandial lipemia and appetite sensation in young men," Nutrition, Metabolism & Cardiovascular Diseases, 2011, pp. 1-8.
Kristensen, Mette et al., "Flaxseed dietary fibers lower cholesterol and increas fecal fat excretion, but magnitude of effect depend on food type," Nutrition and Metabolism, 2012, vol. 9, pp. 1-8.
Cui et al., "Chemical Structure, Molecular Size Distributions, and Rheological Properties of Flaxseed Gum," J. Agric. Food Chem., 1994, vol. 42, pp. 1891-1895.
Oomah et al., "Variation in the Composition of Water-Soluble Polysaccharides in Flaxseed," J. Agric. Food Chem., 1995, vol. 43, pp. 1484-1488.
European Food Safety Authority (EFSA) Panel on Dietetic Products, Nutrition and Allergies, Scientific Opinion on the Substantiation of Health Claims Related to Dietary Fibre, EFSA Journal 2010, vol. 8, Issue 10, p. 1735 [23 pp.].
Miller III, E.R. et al., "The Effects of Macronutrients on Blood Pressure and Lipids: An Overview of the DASH and OmniHeart Trials," Current Atherosclerosis Reports 2006, vol. 8, pp. 460-465.
Katan, M.B. et al., "Effects of fats and fatty acids on blood lipids in humans, an overview," Am. J. Clin. Nutr., 1994, vol. 60(suppl.), pp. 1017S-1022S.
Ascherio, A., "Trans fatty acids and blood lipids," Artherosclerosis Supplements, 2006, vol. 7, pp. 25-27.
Jenkins, D.J.A. et al., "Low glycemic index carbohydrate foods in the management of hyperlipidemia," The American Journal of Clinical Nutrition, Oct. 1985, vol. 42, pp. 604-617.
Jenkins, D.J.A., "Dietary Fibre, Diabetes, and Hyperlipidemia—Process and Prospects," The Lancet, Dec. 15, 1979, pp. 1287-1290.
Wanders, A.J. et al., "Effects of dietary fibre on subjective appetite, energy intake and body weight: a systematic review of randomized controlled trials," Obesity Reviews, 2011, [16 pp.].
Warrand, J. et al., "Contributions of Intermolecular Interactions between Constitutive Arabinoxylans to the Flaxseeds Mucilage Properties," Biomacromolecules 2005, vol. 6, pp. 1871-1876.
Tarpita et al., "Flaxseed as a functional food," Current Topics in Nutraceutical Research, 2005, vol. 3, No. 3, pp. 167-188.
Krotkiewski, "Effects of a galactomannan-based preparation on satiety, hunger, and food preferences in obese women observing a hypocaloric diet of 1100 kcal/day," Cahiers de Nutrition et de Dietetique, 1992, vol. 27, No. 4, pp. 211-217.
Mazza, et al., "Flaxseed, dietary fiber, and cyanogens," Flaxseed in human nutrition, Editors, Stephen C. et al., AOCS Press, Champaign, IL, 1995, pp. 56-81.
Alzueta, C. et al., "Effect of whole and demucilaged linseed in broiler chicken diets on digesta viscosity, nutrient utilization and intestinal microflora," British Poultry Science, 2003, vol. 44, pp. 67-74.
Kempe, R. et al., "Effect of linseed cake supplementation on digestibility and faecal and haematological parameters in dogs," Journal of Animal Physiology and Animal Nutrition, 2007, vol. 91, pp. 319-325.
Kristensen, Mette, "Wholegrains and dietary fibres—Impact on body weight, appetite regulation and nutrient digestibility," PhD Thesis, Department of Human Nutrition, Faculty of Life Sciences, University of Copenhagen, Denmark 2009.
Thakur, Goutam et al., "Effect of flaxseed gum on reduction of blood glucose and cholesterol in type 2 diabetic patients," International Journal of Food Sciences and Nutrition, 2009, pp. 1-11.
Trunbull, W.H. et al., "The effect of a Plantago ovata seed containing preparation on appetite variables, nurtient and energy intake," International Journal of Obesity, 1995, vol. 19, pp. 338-342.

(56) References Cited

OTHER PUBLICATIONS

Bansall, Sandeep et al., "Fasting Compared with Nonfasting Triglycerides and Risk of Cardiovascular Events in Women," JAMA, Jul. 18, 2007, vol. 298, No. 3, pp. 309-316.
Bellisle, F., "Functional Foods and the Satiety Cascade," British Nutrition Foundation, 2008, vol. 33, pp. 8-14.
Bhathena et al., "Effects of dietary soybean and flaxseed meal on metabolic parameters in a genetic model of obesity and diabetes," Experimental Biology, 2002: Meeting Abstracts, p. A1013, XP008050724.
Bligh et al., "A rapid method of total lipid extraction and purification," Canadian Journal of Biochemistry and Physiology, 1959, vol. 37, No. 8, pp. 911-917.
Brændegaard, Mikkelsen, Euroman, Mar. 2003, No. 109, pp. 138-139.
Crespo, N. et al., "Dietary Polyunsaturated Fatty Acids Decrease Fat Deposition in Separable Fat Depots but Not in the Remainder Carcass," Poultry Science, Apr. 2002, vol. 81, No. 4, pp. 512-518.
Crespo, N. et al., "Nutrient and Fatty Acid Deposition in Broilers Fed Different Dietary Fatty Acid Profiles," Poultry Science, Oct. 2002, vol. 81, No. 10, pp. 1533-1542.
Cummings et al., "Transit through the gut measured by analysis of a single stool," Gut, 1976, vol. 17, pp. 219-223.
Cunnane et al., "High α-linolenic acid flaxseed (*Linum usitatissimum*): Some nutritional properties in humans," British Journal of Nutrition, 1993, vol. 69, pp. 443-453.
Flint, A. et al., "Reproducibiolity, power and validity of visual analogue scales in assessment of appetite sensations in single test meal studies," International Journal of Obesity, 2000, vol. 24, pp. 38-48.
Forbrugernyt, "Something to Munch On," Samvirke, Nov. 2003, vol. 26, No. 11, pp. 112.
Frotz et al., "Die Veränderungen des Stuhifettsäuremusters nach Leinölbelastung und ihr diagnostischer Wert zur Beurteilung der Fetttresoprtion," Varhandlungen der Deutchen Gesellschaft fur innere medizin, 1969, vol. 75, pp. 666-669.
Hansen et al., "The Nutritional Influence of Flax Seed and Sunflower Seeds in Rye Bread," Tine Worm Damgaards, Sep. 17, 2002, pp. 1-4.
Kleiber, M., "The fire of Life: An Introduction to Animal Energetics," New York, John Wiley, 1987, pp. 259-264.
Knudsen, K.E.B., "Carbohydrate and lignin contents of plant materials used in animal feeding," Animal Feed Science Technology, 1997, vol. 67, pp. 319-338.
Livesey, G., "Procedure for calculating the digestibel and metabolisable energy values of food components making a small contribution to dietary intake," J. Sci. food Agric., 1989, vol. 48, pp. 475-481.
Livesey, G., "Energy values of unavailable carbohydrate and diets: An inquiry and analysis," Am. J. Clin, Nutr., 1990, vol. 51, pp. 617-637.
Lucas et al., "Flaxseed reduces plasma cholesterol and atherosclerotic lesion formation in ovariectomized Golden Syrian hamsters," Atherosclerosis, 2004, vol. 173, pp. 223-229.
Madhusudhan et al., "Effect of heat treatment on the functional properties of linseed meal," J. Agric. Food Chem., 1985, vol. 33, pp. 1222-1226.
Oohmah, B. Dave et al., "Fractionation of flaxseed with a batch dehuller," Industrial Crops and Products, 1998, vol. 9, pp. 19-27.
Oomah, B. Dave et al, "Health benefits of phytochemicals from selected Canadian crops," Trend in food Science and Technology, 1999, vol. 10, pp. 193-198.
Oomah, B.D., "Flaxseed as a functional food source," Journal of the Science of Food and Agriculture, 2001, vol. 81, pp. 889-894.
Ortiz et al., "Metabolisable energy value and digestibility of fat and fatty acids in linseed determined with growing broiler chickens," British Poultry Science, 2001, vol. 42, pp. 57-63.
Hollander, P; "Orlistat in the Treatment of Obesity", Primary Care, Saunders, London, GB, vol. 30, No. 2, Jan. 1, 2003, pp. 427-440.
Enzi G. et al. Effect of a hydrophilic mucilage in the treatment of obese patients. Pharmatherapeutica. 1980;2(7):421-8.

\* cited by examiner

COMPOSITIONS AND METHODS FOR INCREASING THE SUPPRESSION OF HUNGER AND REDUCING THE DIGESTIBILITY OF NON-FAT ENERGY SATIETY

CROSS REFERENCE TO RELATED APPLICATIONS

This application is a continuation of Ser. No. 12/676,583, filed on May 11, 2010, which is the U.S. national phase application of PCT/DK2008/000321, filed on Sep. 12, 2008, which claims priority to Danish Patent Application No. PA 2007 01320, filed on Sep. 12, 2007, U.S. Provisional Application No. 60/971,798, filed on Sep. 12, 2007, Danish Patent Application No. PA 2007 01319, filed on Sep. 12, 2007, and U.S. Provisional Application No. 60/971,827, filed on Sep. 12, 2007. The disclosures of the above-referenced applications are hereby incorporated by reference in their entireties.

TECHNICAL FIELD OF THE INVENTION

The present invention relates to methods, feed, food and beverage ingredients and dietary supplements effective for increasing the suppression of hunger and/or increasing the reduction of prospective consumption and/or increasing the reduction of appetite and/or increasing the feeling of satiety and managing body weight i.e. prevention of a positive energy balance, weight gain and overweight, treatment of overweight and obesity as well as weight reduction for cosmetic purposes. In particular, the feed, food and beverage ingredient and dietary supplements of the present invention comprises mucilage and/or one or more active compounds thereof useful for increasing the suppression of hunger and/or increasing the reduction of prospective consumption and/or increasing the reduction of appetite and/or promoting, and/or increasing and/or prolonging satiety, reducing non-fat energy uptake in the gastrointestinal tract and thus to induce a negative energy balance and weight loss in subjects who wish to reduce their body weight.

BACKGROUND OF THE INVENTION

The current way of life in industrialised countries may be characterised by less physical work and increased consumption of fat, carbohydrates and proteins, resulting in the energy intake exceeding energy expenditure. This shift in the energy balance causes storage of energy in the body in form of fat, leading to an increase of overweight and obesity, due to the long-term energy imbalance associated with lifestyle.

The percentage of overweight people increases year by year and obesity is a disease that is reaching epidemic proportions in some countries. The health risks associated with overweight and obesity are numerous and it has been shown that these conditions contribute to morbidity and mortality of individuals suffering from diseases such as hypertension, stroke, diabetes mellitus type II, gallbladder disease and ischaemic heart disease. The cosmetic perspective of body fat is also to be considered as the demand for dietary supplements or medicine to gain or maintain a leaner body is constantly increasing.

A common strategy for reducing weight or for maintaining a normal body weight has been to reduce the average energy intake by lowering the dietary fat intake. Numerous low fat, no fat, reduced fat and "light" types of feed, food and beverage products and diets have appeared on the marked. However, the overall energy content of such products are often the same as in traditional feed, food and beverage products, because the content of carbohydrates, such as sugars, in such low fat products is increased in order to compensate for the fat with regard to taste and structure.

To assist in weight loss some people choose to limit their food energy intake by substituting the sugar with other sweeteners with little or no energy, the so-called diet products. Often, the traditional sugar in such products is substituted with artificial sweeteners such as high intensity sweeteners. This allows the consumer to eat the same foods they would normally do while allowing them to lose weight and avoid other problems associated with excessive energy intake. However, studies have shown that, rather than promoting weight loss, the use of e.g. diet drinks resulted in increasing weight gain and obesity.

Thus, although there are numerous products on the marked which intend to assist individuals in loosing weight, the prevalence of overweight and obesity has continued to increase. One of many reasons for this might be that the low fat and diet products are far too often abandoned by the individual due to a reduced taste sensation, palatability and/or structure.

An additional factor which may lead to overweight or mal-nutrition is the busy modern lifestyle. Often people resort to eating less wholesome fast-food for the sake of convenience, for instance when there is no time to prepare a healthy home cooked meal. In particular, such fast-food products are often too rich in fat and carbohydrates.

An alternative approach to improving the management of body weight and overall health would be the development of functional foods, food ingredients and dietary supplements, which would assist in reducing the incentive to eat and/or postponing the need to eat until a proper meal is available. Development of such products would be greatly facilitated by the identification of substances having the ability of reducing or postponing the sensation of hunger and/or appetite and perhaps at the same time being able to increase or prolong the feeling of satiety, In order to be successful, such functional foods must have similar qualities in terms of palatability, taste and structure as traditional foods. Similarly, it is imperative that such dietary supplements and food ingredients do not negatively affect the quality of the diet or the food products. Accordingly, there is a great need for identifying substances having such qualities while being suitable for consumption.

SUMMARY OF THE INVENTION

The present inventors found that administration of an effective amount of mucilage and/or one or more active compounds thereof, in particular mucilage from flaxseed, is surprisingly effective in increasing the suppression of hunger and increasing the reduction of prospective consumption and increasing the reduction of appetite and increasing the feeling of satiety of a subject. In addition, administration of an effective amount of mucilage and/or one or more active compounds thereof, in particular mucilage from flaxseed, is efficient in reducing digestibility of non-fat energy in the gastrointestinal tract of a mammal and thus prevents a positive energy balance, weight gain, overweight and obesity, and to induce a negative energy balance and weight loss in subjects who wish to reduce their body weight. Thus, the demonstrated effect of the present mucilage and the possibility of formulating the mucilage in various ways offers obvious possibilities of using mucilage and/or one or more active compounds thereof for the management of body weight.

Thus, an object of the present invention relates to the use of mucilage and/or one or more active compounds thereof in the preparation of a feed, food and/or beverage product for increasing the suppression of hunger and/or increasing the reduction of prospective consumption and/or increasing the reduction of appetite and/or promoting and/or increasing and/or prolonging the feeling of satiety. It further relates to an alternative feed, food and beverage ingredient and dietary supplement useful for preventing non-fat energy over-consumption and thus weight gain.

Accordingly, the present invention provides uses, methods, feed, food and/or beverage product and ingredients and dietary supplements comprising mucilage and/or one or more active compounds thereof useful for increasing the suppression of hunger and/or increasing the reduction of prospective consumption and/or increasing the reduction of appetite and/or promoting and/or increasing and/or prolonging the feeling of satiety and/or reducing the digestibility of non-fat energy from the gastrointestinal tract in mammals including humans.

Thus, one aspect of the invention relates to the use of mucilage and/or one or more active components thereof in the preparation of a dietary supplement and/or a food ingredient and/or a feed, food and/or beverage product for increased suppression of hunger and/or increased reduction of prospective consumption and/or increased reduction of appetite in a subject during and/or between meals or feedings comprising said dietary supplement and/or said food ingredient and/or said feed, food and/or beverage product.

A further aspect relates to a method of increasing the suppression of hunger and/or increasing the reduction of prospective consumption and/or increasing the reduction of appetite in a subject during and/or between a meal or a feeding, said method comprising administrating to said subject, in connection with said meal or feeding or as part of said meal or feeding, flax seed mucilage and/or one or more active components thereof.

It also relates to mucilage and/or one or more active components thereof for use in increasing suppression of hunger and/or increasing reduction of prospective consumption and/or increasing reduction of appetite.

A still further aspect relates to the use of mucilage and/or one or more active components thereof as a feed, food or beverage ingredient, dietary supplement or fortificant or food ingredient for increasing suppression of hunger and/or increasing reduction of prospective consumption and/or increasing reduction of appetite.

Further, the present invention relates to mucilage and/or one or more active components thereof for use as a supplement for ingestion in combination with a pharmaceutical product comprising an inhibitor of GI-tract activities and/or an inhibitor of a pancreatic lipase.

A further aspect pertains to a feed, food and/or beverage product having a fat content that provides up to, but not including, 10% of the total energy content of said feed, food and/or beverage product or dietary supplement, comprising mucilage and/or one or more active components thereof.

Moreover, the present invention relates to a feed, food and/or beverage product comprising mucilage and/or one or more active compounds thereof and an artificial fat.

The present invention also relates to a non-fat feed, food and/or beverage product or dietary supplement comprising mucilage and/or one or more active components thereof.

DETAILED DESCRIPTION OF THE INVENTION

Definitions

Figure 1:
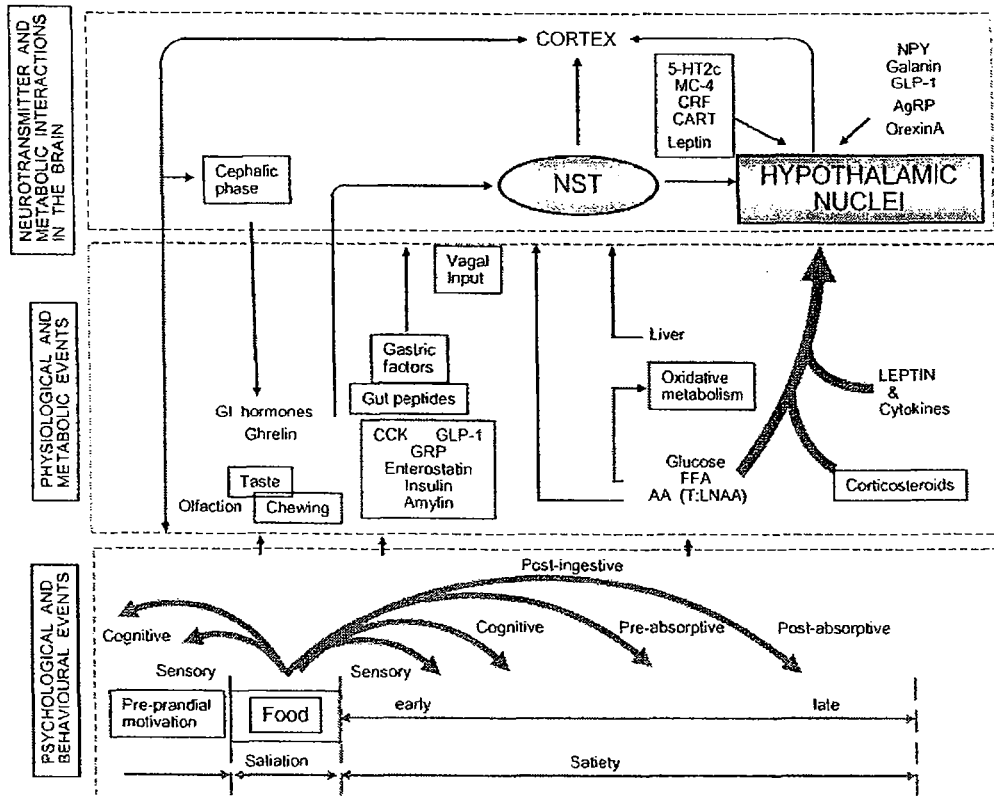
FIG. 1 shows the 'satiety cascade' viewed from a behavioural perspective (lowest level), in terms of peripheral physiological and metabolic events (middle level), and in terms of brain responses (top level). 5-HT, serotonin; AA, amino acids; AgRP, Agouti related peptide; CART, cocaine and amphetamine regulated transcript; CCK, cholecystokinin; CRF, corticotropin releasing factor; FFA, free fatty acids; GI, gastrointestinal; GLP-1, glucagon like peptide-1, GRP, gastric releasing peptide; MC, melanocortin; NPY, neuropeptide Y; NST, nucleus tractus solitarius; T:LNAA, tryptophan : large neutral amino acid ratio (from Bellisle, 2008)

Prior to discussing the present invention in further details, the following terms and conventions will first be defined:

In the present context the term "mucilage" or "fibres from mucilage" relates to a type of dietary fibres produced by some plants and is present on the outside of the seed coat. The mucilage is a group of heterogenic, water-soluble polysaccharides comprising "active compounds" mainly arabinoxylans (pentosans) and galacturonic acid, but also plant lignans, such as glycosides of secoisolariciresinol as the major plant-lignan, together with smaller amounts of matairesinol, isolariciresinol, and pinoresinol. Without being limited by theory, it is contemplated that part of the non-fat energy retaining capacity of the mucilage is a result of one or more of the above active compounds of the mucilage. It is hypothesised that a binding may take place between one or more of the active compounds of the mucilage and the non-fat energy in the gastrointestinal tract, thereby reducing the overall digestibility of non-fat energy.

Dietary fibres are the indigestible portion of the plant and consist of non-starch polysaccharides such as cellulose, hemicellulose and many other plant components such as arabinoxylans, betaglucans, fructo- and galactooligosaccharides, pectins, lignins, waxes and chitins. For practical purposes dietary fibres may be divided into water-soluble and water insoluble fibres.

"Appetite regulation" is a general term used to describe the regulation of energy intake to match expenditure and should be thought of as a redundant system, meaning a system of overlapping subsystems which do not all need to be functioning optimally for the overall system to work. Following a meal, various signals originating from the gastrointestinal tract inform the brain that food is being processed. Such signals can be neural or hormonal in nature. They represent the 'post-ingestive' signals of the satiety cascade. Finally, after nutrients become available to peripheral and brain tissues, post-absorptive signals maintain satiety until the fuel brought by the previous meal has been utilised and/or stored. Usually, towards the end of this phase, hunger signals inform the brain that more energy sources should be found, acquired and ingested. This is the end of the 'satiety cascade' and the beginning of a new ingestive episode.

In the context of appetite regulation "hunger" is the biological drive that impels the ingestion of food. Hunger sensation is controlled to a large extent by hormonal regulation. For instance, the fluctuation of leptin and ghrelin hormone levels results in the motivation of an organism to consume food. When an organism eats, adipocytes trigger the release of leptin into the body. Increasing levels of leptin results in a reduction of one's motivation to eat. After hours of non-consumption, leptin levels drop significantly. These low levels of leptin cause the release of secondary hormone, ghrelin, which in turn reinitiates the feeling of hunger.

"Ghrelin" is a 28-amino acid peptide is synthesized principally in the stomach. Plasma ghrelin levels were first noted to increase on fasting and fall on refeeding in rodents, as would befit a hunger signal. Studies have demonstrated that plasma ghrelin also peaks preprandially in human subjects, who have been deprived of time cues, initiating meals voluntarily. These plasma ghrelin peaks correlated well with hunger scores. Postprandially, plasma ghrelin is suppressed in proportion to calories ingested.

The expression "prospective consumption" relates in the present context to a measure of appetite. It is defined as the amount of food which a given subject feels likely to eat.

In the context of the present invention, hunger, satiety, fullness, prospective food consumption is conveniently assessed by using visual analogue scales (VAS) as described in Flint et al. 2000.

In the context of the present invention the term "appetite" is defined as the desire to eat food, felt as hunger.

For the present purpose the term "satiety" (intermeal satiety) defines the sensation of fullness between eating episodes that tends to inhibit the resumption of eating, but is also commonly used to refer to both intra- and intermeal satiety combined.

The term "postprandial" means after eating a meal. In the present context the term in particular defines the period in time starting immediately after ingestion of a meal and until ingestion of a following meal commences.

The term "absorptive phase" refers to the phase during which ingested nutrients are entering the blood from gastrointestinal tract.

The term "postabsorptive phase" is conventionally defined as the state during which the gastrointestinal tract is empty of nutrients and energy must be supplied by the body's own stores. Since an average meal requires approximately 4 hours for complete absorption, a usual three-meal-a-day pattern places a subject in the postabsorptive phase during the late morning and afternoon and almost the entire night.

A "gastrointestinal hormone" is a hormone secreted by enteroendocrine cells in the stomach, pancreas, and small intestine that controls various functions of the digestive organs. Based on their chemical structure the gastrointestinal hormones can be divided into three main groups:

I. Gastrin-cholecystokinin family, including gastrin and cholecystokinin

II. Secretin family, including secretin, glucagon, vasoactive intestinal peptide and gastric inhibitory peptide III. Peptide family, including somatostatin, motilin and substance P.

The terms "non-fat energy" and "non-fat calories" relates to the energy from carbohydrates and proteins from the mucilage and/or one or more active compounds thereof or from the feed, food and/or beverage product ingested prior, concomitantly or immediately after said mucilage and/or one or more active compounds thereof, which is available through digestion. The values for energy are expressed in kilocalories (kcal) and kilojoules (kJ) or mega joules (MJ). In accordance with the present invention, the gross energy contained in the faecal excrements of a mammal is measured by being completely burned in a calorimeter so that the heat released through combustion can be accurately measured. The faecal fat is measured directly by appropriate chemical analysis and this amount is multiplied an energy factor for fat (39 kJ/g) which is subtracted from the gross energy. The remainder energy is comprised by non-fat energy—equivalent to energy from protein and carbohydrates.

In the present context the term "management of body weight" covers all aspect of modulating the body weight for maintenance or achievement of a "desirable weight". In contrast to the "desirable weight" the expressions "overweight" and "obesity" are used as indications of a body with a weight exceeding the "desirable weight".

The "desirable weight", "normal weight" or "optimal weight" for humans may be defined according to standards such as Body Mass Index (BMI), which is a common measure expressing the relationship (or ratio) of weight-to-height (for definition see below). The BMI is more highly correlated with body fat than any other simple measure of height and weight. Desirable BMI levels may vary with age, but a "normal" BMI is considered to be in the range of 18.5-24.9.

The definition of "overweight" is an increased body weight in relation to height, when compared to a standard of acceptable or desirable weight. Individuals with BMI in the range of 25-29.9 are considered to be overweight.

Obesity is a multi-factorial disease involving an accumulation of excess adipose tissue (fat) sufficient to harm health. As stated, overweight and obesity cause the development of several diseases and individuals suffering from overweight or obesity generally have a poor health status. Obesity is largely preventable through changes in lifestyle, especially diet, however, real treatment may be desired and needed to aid in loosing of weight.

There are many types of obesity, but it is most commonly assessed by a single measure, the Body Mass Index (BMI) a ratio of weight and height (BMI=weight (kg)/height (m)$^2$). The World Health Organization classifies underweight, normal weight, overweight and obesity according to categories of BMI (cf. table below). This height independent measure of weight allows comparisons to be made more readily within and between populations. The BMI value, however, neither distinguish fat from lean tissue nor identify whether the fat is laid down in particular sites e.g., abdominally where it has more serious consequences.

Waist circumference measurement is also increasingly recognised as a simple means of identifying abdominal obesity. Body fat distribution can be estimated by skinfold measures, waist-to-hip circumference ratios, or techniques such as ultrasound, computed tomography, or magnetic resonance imaging.

TABLE 1

| Classification | BMI (kg/m$^2$) | Risk of co-morbidities |
| --- | --- | --- |
| Underweight | <18.5 | Low (but risk of other clinical problems increased) |
| Normal range | 18.5-24.9 | Average |
| Overweight* | ≥25 | |
| Pre-obese | 25.0-29.9 | Mildly increased |
| Obese | >30.0 | |
| Class I | 30.0-34.9 | Moderate |
| Class II | 35.0-39.9 | Severe |
| Class III | >40.0 | Very severe |

*The term overweight refers to a BMI ≥25, but is frequently and also in the present specification and claims adapted to refer to the BMI 25-29.9, differentiating the pre-obese from the obese categories As illustrated in Table 1 above, the severities of obesity may by classified by ranges of BMI where BMI in the range of 30-34.9 is classified as moderate obesity, BMI in the range of 35-39.9 is classified as severe obesity and BMI over 40 is classified as very severe obesity. The definition of obesity may also include taking in account both the distribution of fat throughout the body and the size of the adipose tissue deposits.

Individuals falling under the above characterisation as "obese" are far more susceptible to health implications as a consequence of their overweight. Several serious medical conditions have been linked to obesity, including type 2 diabetes, heart disease, high blood pressure, and stroke. Obesity is also linked to higher rates of certain types of cancer. Obese men are more likely than non-obese men to die from cancer of the colon, rectum, or prostate. Obese women are more likely than non-obese women to die from cancer of the gallbladder, breast, uterus, cervix, or ovaries. Other diseases and health problems linked to obesity include gallbladder disease and gallstones, liver disease, osteoarthritis, a disease in which the joints deteriorate possibly as a result of excess weight on the joints, gout, another disease affecting the joints, pulmonary (breathing) problems, including sleep apnea in which a person can stop breathing for a short time during sleep, reproductive problems in women, including menstrual irregularities and infertility. Health care providers generally agree that the more obese a person is the more likely he or she is to develop health problems.

The expression "cosmetic overweight" refers to a weight that does not have any immediately medical implications on the individual but may be in a range that is not satisfactory for cosmetic reasons. As fashion with respect to body size changes some individuals may interpret the "normal weight" as "cosmetic overweight". As a consequence such individuals may have a desire of treating cosmetic overweight.

The expression "digestibility of non-fat energy" is used herein interchangeably with the expression "utilisation of non-fat energy" and relates to the utilisation of non-fat energy, originating from the instant mucilage or from the concomitantly ingested feed, food and/or beverage product, in a mammal. "Digestibility of non-fat energy" and "utilisation of non-fat energy" is expressed relative to the amount of the non-fat energy intake, such as % of daily intake. Furthermore, the terms "absorption of non-fat energy" and "uptake of non-fat energy" are used interchangeably and relate to the absolute value (e.g. g/day) of the utilisation of non-fat energy.

In the present context the expressions "reduced digestibility of non-fat energy", "increased excretion of non-fat energy" and "reduced non-fat energy retaining capacity" are used to address the characteristics of the mucilage and/or one or more active compounds of the mucilage. The characteristics of the mucilage and/or one or more active compounds thereof may also be described as "reduced carbohydrate and/or protein digestibility" or as "reduced absorption of non-fat energy in the intestinal tract".

The increased excretion of non-fat energy is conveniently measured by comparing faecal excretion in individuals given a diet comprising the mucilage and/or one or more active compounds thereof with a control group given a similar diet without the mucilage and/or one or more active compounds thereof. The non-fat energy retaining effect of the mucilage and/or one or more active compounds thereof may be quantified by calculating the partial digestible energy value as defined hereinafter.

The term "partial digestible non-fat energy value" used herein refers to differences in overall digestible nutrients when a supplement is added to a basal diet. The calculation of the partial digestible energy values for unavailable carbohydrates in a number of human diets has been found to be in the range from −20 to +10 kJ/g unavailable carbohydrates. Negative values may refer to the additional losses of especially carbohydrates, protein and fat to faeces associated with diets high in unavailable carbohydrates. The partial digestibility is calculated from two feeding trials with and without the active substance as the difference in digestible energy between the two rations divided by the difference in total energy intake.

The term "bulking effect" is used herein to refer to the physiological effect of dietary fibre intake on digestion and satiety. Soluble dietary or complex fibres increase many times in volume when they mix with fluid and therefore promote satiety. Bulking agents such as polydextrose are additives that increase the bulk of a food without affecting its nutritional value. The total bulking effect is known to decrease energy intake by contributing to fullness or satiation and maintaining between meals a feeling of satiety.

The term "fibre effect" relates to the capability of dietary fibres of decreasing the transit time (mouth to anus) of ingested feed, food and/or beverages in the intestinal tract and to decrease the digestibility of energy. Without being bound by theory, it is contemplated that the decreased digestibility of energy resulting from the fibre effect would counteract the feeling of satiety resulting from the bulking effect.

As shown in the below examples, it was found that despite the counteracting effects of the bulking effect and the fibre effect on satiety, subjects did in fact experience significantly increased suppression of hunger, increased reduction of prospective consumption, increased reduction of appetite and increased satiety after ingestion of a meal fortified or supplemented with mucilage and/or one or more active component thereof. It is contemplated that an active component of the mucilage is affecting the sensation of satiety, hunger, prospective consumption and appetite via signaling pathways in the gastrointestinal tract, in particular in the small intestine. This mechanism appears to be activated independently of the bulking effect caused by the increase in volume of dietary or complex fibres when they mix with fluid.

In addition, it appears that an effect of mucilage fibres from flaxseeds and/or one or more active compounds thereof on the digestibility of non-fat energy (carbohydrates and proteins) is evident even in the absence of a simultaneous effect of the fibres leading to reduced food or feed intake.

In addition, it appears that an effect of mucilage fibres from flaxseeds and/or one or more active compounds thereof highly affected on the digestibility of non-fat energy (carbohydrates and proteins) to a non-expected extent given the fact that no bulking effect could be observed since the amount of the ingested food was similar in the control group and the diet group supplemented with mucilage.

Preferred Embodiments

Flaxseeds are well recognised for their high content of dietary fibre consisting of soluble (9%) and insoluble (20%) fibres. As described above, the soluble fibres are commonly referred to as mucilage and are found mainly in the epidermal layers of the seed coat, which makes up most of the hull.

The mucilage of flaxseeds has been identified as the most abundant source of plant lignans, such as glycosides of secoisolariciresinol as the major lignan, together with small amounts of matairesinol, isolariciresinol, and pinoresinol, making the dietary intake of flaxseeds of interest from a health promoting point of view. Due to its gelation properties, mucilage from flaxseeds has also been used in some food products for thickening liquids.

In an earlier study, disclosed in WO 2005/107777, the present inventors used flaxseed, in particular hydrated and/or heat treated whole flaxseeds, in methods for increasing faecal fat excretion from the gastrointestinal tract of a mammal in order to achive a negative energy balance and thus to prevent weight gain, overweight and obesity.

Now the present inventors surprisingly found that fibres from flaxseed mucilage and/or one or more active compounds thereof have a pronounced effect on hunger, prospective consumption, appetite and satiety which appears to be independent on the so-called bulking effect. It also results in impairment on the utilisation of carbohydrates and proteins, i.e. non-fat energy, originating from the mucilage and from the feed, food and/or beverage ingested prior, concomitantly or immediately after said mucilage and/or one or more active compounds thereof. When using mucilage and/or one or more active compounds thereof an increase of total energy excretion was found, which could not be ascribed to an increased fat excretion alone. Although fibres of whole flaxseeds have been shown to have a high affinity to lipids, it has until now not be shown that other nutritive components also are affected by the addition of mucilage fibres to the diet.

Thus, mucilage and/or one or more active compounds of mucilage, when used according to the present invention, reduces the digestibility of non-fat energy and increases faecal excretion of non-fat energy, i.e. reduce uptake of non-fat energy in the intestinal tract, and thus prevents a positive non-fat energy balance and/or induces a negative non-fat energy balance in the subjects who wish to reduce their body weight, as described below.

In certain relations, mucilage was found to be surprisingly more effective that whole flaxseeds. The inventors have observed that the glucose response and acute response of insulin after a meal is reduced by the presence of fibres from flaxseed mucilage in the meal, whereas the feeling of satiety is prolonged, the suppression of hunger, the reduction of prospective consumption and the reduction of appetite is increased. Furthermore, both in terms of the glucose and the insulin responses and satiety, the mucilage appeared to have a greater effect than whole flaxseeds when given in comparable doses. This indicates that the extracted mucilage fibres are more efficient than when the fibres are eaten in its normal matrix.

In addition, mucilage reduced the prostprandial triglyceride response significantly. In this context, it is interesting that a recent study by Bansal et al. 2007 established an association of nonfasting triglyceride levels with incident cardiovascular events in a cohort of initially healthy women. The association was seen independently of traditional cardiac risk factors. Thus, according to the present invention, mucilage and/or one or more active compounds thereof may also be used for preventing cardiovascular diseases or for reducing the incidence of cardiovascular diseases, e.g. atherosclerosis.

These findings provided basis for use of mucilage and/or one or more active compounds thereof for overall management of body weight including the treatment and prevention of overweight in mammals such as humans. In the present context, the term "prevention" means that the use of a mucilage and/or one or more active compounds thereof counteracts the start of overweight and obesity, or counteracts a positive non-fat energy balance leading to weight gain, or that overweight and obesity at least develop to a minor degree in a subject ingesting a mucilage and/or one or more active compounds thereof compared to a subject not ingesting a mucilage and/or one or more active compounds thereof.

As stated above, a first aspect of the present invention relates to the use of mucilage and/or one or more active components thereof in the preparation of a dietary supplement and/or a food ingredient and/or a feed, food and/or beverage product for increased suppression of hunger and/or increased reduction of prospective consumption and/or increased reduction of appetite in a subject during and/or between meals or feedings comprising said dietary supplement and/or said food ingredient and/or said feed, food and/or beverage product.

The invention also relates to the use of mucilage and/or one or more active components thereof in the preparation of a dietary supplement and/or a food ingredient and/or a feed, food and/or beverage product for increased suppression of hunger and/or increased reduction of prospective consumption and/or increased reduction of appetite during and/or after digestion of said dietary supplement and/or food ingredient and/or feed, food and/or beverage product.

The invention further provides the use of mucilage and/or one or more active components thereof in the preparation of a dietary supplement and/or a food ingredient and/or a feed, food and/or beverage product for increased suppression of hunger and/or increased reduction of prospective consumption and/or increased reduction of appetite in a subject after a meal or a feeding comprising said dietary supplement, and/or said food ingredient and/or said feed, food and/or beverage product.

The present invention relates furthermore to the use of mucilage and/or one or more active components thereof in the preparation of a dietary supplement and/or a food ingredient and/or a feed, food and/or beverage product for increased suppression of hunger and/or increased reduction of prospective consumption and/or increased reduction of appetite in a subject the post-ingestive phase (such as in the sensory, cognitive, pre-absorptive, absorptive and/or post-absorptive phase) after a meal or feeding comprising said dietary supplement and/or said food ingredient, and/or said feed, food and/or beverage product.

The uses of the above dietary supplement and/or food ingredient and/or a feed, food and/or beverage product are also for obtaining an increased promotion and/or prolongation of the feeling of satiety.

Furthermore, in relation to all aspect according to the invention the use of mucilage and/or one or more active components thereof as provided herein is preferably for obtaining improved management of body weight, such as decreased body weight or maintenance of body weight.

A further aspect relates to a method of increasing the suppression of hunger and/or increasing the reduction of prospective consumption and/or increasing the reduction of appetite in a subject during and/or between a meal or a feeding, said method comprising administrating to said subject, in connection with said meal or feeding or as part of said meal or feeding, flax seed mucilage and/or one or more active components thereof.

In a useful embodiment, the present method further comprises a step of assessing and/or measuring a parameter selected from the group consisting of hunger, appetite, satiety, and prospective consumption.

In an additional embodiment, the method further comprises a step of measuring altered secretion and/or altered blood or plasma levels and/or altered activity of a factor selected from the group consisting of a gastrointestinal hormone, a gastric factor, a gut peptide, cholecystokinin (CCK), glucagon like peptide-1 (GLP-1) and gastric releasing peptide (GRP), peptide YY and combinations thereof.

In one embodiment, the method of the present invention is also for obtaining an increased promotion and/or prolongation of the feeling of satiety.

Said method in accordance with the present invention may further comprise a step of identifying a subject in need for increased suppression of hunger and/or increased reduction of prospective consumption and/or increased reduction of appetite and/or increased and/or prolonged satiety.

In present invention also relates to the use of mucilage and/or one or more active compounds of mucilage in the preparation of a feed, food and/or beverage product for reducing the digestibility of non-fat energy in the intestinal tract in a mammal, wherein the non-fat energy originates from said mucilage, said food and/or beverage product and/or other foods and/or beverages ingested prior, concomitantly or immediately after said mucilage and/or one or more active compounds thereof and/or one or more active compounds thereof. It further provides the use of mucilage and/or one or more active compounds thereof in the preparation of a feed, food and/or beverage product for promoting and/or increasing and/or prolonging the feeling of satiety.

As will be apparent, preferred features, characteristics and embodiments of one aspect of the present invention may be applicable to other aspects of the present invention.

Accordingly, in preferred embodiments of the above uses and method, the suppression of hunger and/or reduction of prospective consumption and/or reduction of appetite is increased as compared to the suppression during and/or after digestion of an isocaloric amount of a comparable dietary supplement and/or food ingredient feed and/or food or beverage product which does not comprise flaxseed mucilage or one or more active components thereof.

The dietary supplements or food ingredients or feed, food or beverage products are in a useful embodiment comparable with regard to their relative and absolute content of carbohydrates, lipids and protein.

Based on the examples below, the suppression of hunger and/or reduction of appetite may be increased by at least 5%, when determined as area under the curve (AUC) representing least square means (N=18) of hunger or appetite at 30 minutes intervals during a 420 minute period following consumption of said dietary supplement, feed, food or beverage product. In further embodiments, the suppression of hunger and/or reduction of appetite is increased by at least 10%, such as at least 15%, at least 20%, e.g. at least 25%, such as at least 30%, including at least 35%, e.g. at least 40%. In still further embodiments the suppression of hunger and/or reduction of appetite is increased by 2-10%, such as by 5-15%, by 7-15%, by 10-15%, by 10-20%, by 10-25%, by 12-20%, by 12-25%, by 15-20%, by 15-25% or such as by 20-25%, e.g. by 20-30%.

As further shown in the examples, the suppression of prospective eating is increased by at least 5%, when determined as area under the curve (AUC) representing least square means (N=18) of hunger at 30 minutes intervals during a 420 minute period following consumption of said dietary supplement, feed, food or beverage product. In further embodiments, the suppression of prospective eating is increased by at least 10%, such as at least 15%, at least 20%, e.g. at least 20%, such as at least 25%, including at least 30%, e.g. at least 35%. In still further embodiments the suppression of prospective eating is increased by 2-10%, such as by 5-15%, by 7-15%, by 10-15%, by 10-20%, by 10-25%, by 12-20%, by 12-25%, by 15-20%, by 15-25% or such as by 20-25%, e.g. by 20-30%.

In interesting embodiments, the promotion and/or prolongation of the feeling of satiety is increased by at least 5%, when determined as area under the curve (AUC) representing least square means (N=18) of hunger at 30 minutes intervals during a 420 minute period following consumption of said dietary supplement, feed, food or beverage product. In further embodiments, the promotion and/or prolongation of the feeling of satiety is increased by at least 10%, such as at least 15%, at least 20%, e.g. at least 25%, such as at least 30%, including at least 35%, e.g. at least 40%. In still further embodiments the promotion and/or prolongation of the feeling of satiety is increased by 2-10%, such as by 5-15%, by 7-15%, by 10-15%, by 10-20%, by 10-25%, by 12-20%, by 12-25%, by 15-20%, by 15-25% or such as by 20-25%, e.g. by 20-30%.

In interesting embodiments, the sensation of fullness is increased by at least 5%, when determined as area under the curve (AUC) representing least square means (N=18) of hunger at 30 minutes intervals during a 420 minute period following consumption of said dietary supplement, feed, food or beverage product. In further embodiments, the sensation of fullness is increased by at least 10%, such as at least 15%, at least 20%, e.g. at least 25%, such as at least 30%, including at least 35%, e.g. at least 40%. In still further embodiments the sensation of fullness is increased by 2-10%, such as by 5-15%, by 7-15%, by 10-15%, by 10-20%, by 10-25%, by 12-20%, by 12-25%, by 15-20%, by 15-25% or such as by 20-25%, e.g. by 20-30%.

Means and methods for assessing the influence of mucilage on hunger prospective consumption, appetite, satiety, fullness, gastrointestinal hormones, gastric factors or hormones, gut peptides, cholecystokinin (CCK), glucagon like peptide-1 (GLP-1) and gastric releasing peptide (GRP) are illustrated in Example 3 in the present application and will be well known to the skilled person.

In one embodiment of the present invention the increased suppression of hunger and/or increased reduction of prospective consumption and/or increased reduction of appetite is mediated by altered secretion and/or activity of a factor selected from the group consisting of a gastrointestinal hormone, a gastric factor or hormone such as ghrelin, a gut peptide, cholecystokinin (CCK), glucagon like peptide-1 (GLP-1) and gastric releasing peptide (GRP) and combinations thereof.

The secretion and/or activity of ghrelin may be decreased by at least 5%, when determined as area under the curve (AUC) representing least square means (N=18) of ghrelin at 30 minutes intervals during a 420 minute period following consumption of said dietary supplement, feed, food or beverage product. In further embodiments, the secretion and/or activity of ghrelin is decreased by at least 19%, such as at least 15%, such as at least 20%, including at least 25%, e.g. at least 30%.

Furthermore, the secretion and/or activity of GLP-1 may be increased by at least 1%, when determined as area under the curve (AUC) representing least square means (N=18) of GLP-1 at 30 minutes intervals during a 420 minute period following consumption of said dietary supplement, feed, food or beverage product.

In further embodiments, the secretion and/or activity of ghrelin is decreased by at least 1.5%, such as at least 2.0%, including at least 2.5%, e.g. at least 3.0%.

In a further embodiment of the present invention, the increased suppression of hunger and/or increased reduction of prospective consumption and/or increased reduction of appetite is effectuated while postprandial glycemia and/or lipemia, and/or aminoacidemia is/are either reduced or unaffected. Accordingly, the increased suppression of hunger and/or increased reduction of prospective consumption and/or increased reduction of appetite is effectuated while postprandial blood or plasma glucose levels and/or blood or plasma levels of triacylglycerol (TAG) and/or blood or plasma levels of amino acids is/are either reduced or unaffected.

In accordance with the present invention, the increased suppression of hunger and/or increased reduction of prospective consumption and/or increased reduction of appetite is effectuated while the digestibility of non-fat energy is reduced.

The flax seed mucilage and/or one or more active compounds thereof may be used as an integrated part, such as an ingredient or an fortificant, or as a dietary supplement or additive, of a normal diet, a low fat diet, a low calorie diet or any other diet aiming at managing body weight. The mucilage and/or one or more active compounds thereof may be administered or taken prior, concomitantly or immediately after ingesting a feed, food and/or beverage product and/or a diet. In the present context, the term "concomitantly" means that the mucilage and/or one or more active compounds thereof and the feed, food and/or beverage product are ingested within the same meal, e.g. 0.5-1 hours apart. The term "prior" means in the present context, that mucilage and/or one or more active compounds thereof is ingested or taken at least 1 hour before the feed, food and/or beverage product is ingested, or visa versa. The term "after" or "immediately after" means in the present context, that mucilage and/or one or more active compounds thereof is ingested or taken at least 1 hour after the feed, food and/or beverage product is ingested, or visa versa.

Furthermore, the mucilage and/or one or more active compounds thereof may be used as part of a treatment plan for diabetes, cardiovascular diseases, metabolic syndromes or hyperlipidema. Furthermore, the mucilage and/or one or more active compounds thereof may be prepared as a feed, food and/or beverage product for reducing, in the intestinal tract in a mammal, the digestibility of non-fat energy, from said product and/or other concomitantly ingested feed, foods and/or beverages.

In accordance with the uses and method of the present invention, the use of the mucilage and/or one or more active compounds thereof is preferably directed to a subject such as a human, but any mammal, such as an animal or non-human may also be treated with the mucilage and/or one or more active compounds thereof. In useful embodiments, the animal or non-human may be selected from the group consisting of a dog, a cat, a fish, a bird, a small animal and a horse.

In one embodiment, the use of mucilage and/or one or more active compounds thereof in rats and mice is disclaimed.

In a preferred embodiment, the subject is a human who wishes to reduce his or her body weight. In a further embodiment, the subject is a subjects suffering from overweight, such as cosmetic overweight, or obesity, and are persons having a BMI of at least 25 as shown in the above Table 1. It is contemplated that the method and use of the invention will be particularly beneficial in a subject, who is overweight, non-obese, or obese subject as defined in Table 1.

In an interesting embodiment, the subject is a mammal who wishes to maintain its normal body weight although ingesting high non-fat energy food or feed products. In a further interesting embodiment, the subject is a mammal who wishes to live a healthier life.

In a further interesting embodiment, the subject is an individual which periodically has no or limited or inadequate access to food, such as due to occupational and/or recreational activities. Such individuals may be selected from the group consisting of athletes, emergency or rescue workers and military personnel.

In accordance with the invention, the one or more active compounds of mucilage may be selected from the group consisting of arabinoxylans, galacturonic acid, secoisolariciresinol, matairesinol, isolariciresinol, pinoresinol and combinations thereof.

In a preferred embodiment relating to all aspects of the present invention, the mucilage and/or one or more active components thereof originates from flaxseed (*Linwn. usitatissimum* L.). Useful flaxseed varieties of the genus '*Linum*' from which the mucilage and/or one or more active compounds thereof can be obtained may be selected from the group consisting of Golden, Dufferin, Rahab, Verne, Clark, Culbert, culbert79, Flor, Linott, Linton, McGregor, NorLin, NorMAn and combinations thereof.

It should be noted that the mucilage or the active ingredient of the mucilage may be derived from other plant species. In further embodiments, the mucilage and/or one or more active compounds thereof originates from plant species selected from the group consisting of rye and oat.

As shown in the below examples, the mucilage has a negative partial digestible non-fat energy value, as defined above, when used in accordance with the present invention. In preferred embodiments, the mucilage is characterised by having a negative partial digestible non-fat energy value, in the range of from −1 to −20 kJ/g of the mucilage, including a negative partial digestible non-fat energy value in the range of from −5 to −15 kJ/g, such as in the range of from −10 to −15 kJ/g. Thus, when e.g. supplying the basal diet with mucilage, the faecal excretion of non-fat energy will exceed the non-fat energy intake from the mucilage itself. In other words, a positive non-fat energy balance is prevented and/or a negative non-fat energy balance is induced resulting in a weight loss in subjects who wish to reduce their body weight.

Based on the below examples, if half of the daily recommended intake of dietary fibres, i.e. 15 g, was provided in the form of mucilage, i.e. app. 30 g, an excess excretion of non-fat energy of up to 600 kJ/d can be expected. Thus, in preferred embodiments, the use of mucilage results in an excess excretion of non-fat energy in the range of from 1 to 20 kJ/day/g mucilage, such as in the range of from 5 to 15 kJ/day/g mucilage, such as in the range of from 10 to 15 kJ/day/g mucilage.

Based on the results described below, a recommended daily dose of said dietary supplement or in a food ingredient or in the feed, food and/or beverage product corresponds to an intake of 1 to 45 grams of mucilage/day or 1 to 45 grams of mucilage/5 MJ. Such a dose represents an efficient strategy to increase suppression of hunger and/or to increase reduction of prospective consumption and/or to increase reduction of appetite and/or to prevent energy over-consumption and weight gain. In preferred embodiment, the daily dose of said feed, food and/or beverage product corresponds to an intake of 1 to 40 g, including an intake of 10 to 35 g of mucilage. Typically, the daily dose is equivalent to an amount of about 5 g of mucilage, such as 10 g, 15 g, 20 g, 25 g, 30 g, or 35 g grams of mucilage per day.

The sufficient daily dose for preventing or treating cosmetic overweight or for treatment of medical overweight or obesity as a result of a reduced digestibility of non-fat energy or an increased faecal non-fat energy excretion may vary according to the severity of the overweight/obesity as well as the individual variation and need in order to obtain a desired result.

However, a typical intake for reducing the digestibility of non-fat energy and/or for treatment of overweight or obesity is a dose equivalent to about 1 to 45 g mucilage/day resulting in a loss of faecal non-fat energy from the normal 4-10% of ingested non-fat energy to 15-25%. This corresponds to an additional loss of faecal energy of 375-750 kJ/day, or 300-600 g body weight per month. In the present context, the expression "an additional loss of faecal non-fat energy" relates to a negative partial digestible non-fat energy value, and thus to that the total faecal non-fat energy excretion exceeds the additional non-fat energy intake derived from the mucilage to a considerable extent as described above.

In further embodiments, the total content of mucilage, when used as an ingredient or fortificant, in feed, food and/or beverage product correspond to a content of 1 to 50% of mucilage by weight of the feed, food and/or beverage product, including a content of 1%, 2%, 3%, 4%, 5%, 10%, 15%, 20%, 30% 40% of mucilage by weight of the feed, food and/or beverage product. In useful embodiments, the total content of mucilage when used according to the invention in a feed, food and/or beverage product typically corresponds to a content of 5 to 40%, such as 10 to 30%, including 15-25% of mucilage by weight of the feed, food and/or beverage product.

It will be understood, that when the mucilage and/or one or more active compounds thereof is used as a dietary supplement or food ingredient, the total content of mucilage and/or one or more active compounds thereof correspond to up to 100% by weight of said supplement, such as up to 90%, including up to 80%, such as up to 70% by weight of the supplement. In useful embodiments, the total content of mucilage and/or one or more active components thereof in said food ingredient or in said dietary supplement corresponds to a content of 20 to 100% of mucilage by weight of said food ingredient or dietary supplement, such as 25 to 100%, including 50 to 75%, e.g. 75% to 100%.

In useful embodiments, the feed, food and/or beverage product concomitantly consumed with the mucilage and/or one or more active compounds thereof further comprise ground grains and/or whole grains of one or more of the species selected from the group consisting of sunflower, rye, wheat, maize, soy and combinations thereof.

In an interesting embodiment, said feed, food and/or beverage product or food ingredient or dietary supplement is included in a low fat diet. In the present context, the expression "low fat diet" relates to a diet which fat content is providing only 10-25% of the total energy intake. In particular, the use of mucilage and/or one or more active compounds thereof may be useful in a feed, food and/or beverage having a fat content that provides up to, but not including, 10% of the total energy content of said feed, food and/or beverage product. In useful embodiment, the fat content provides up to 9%, 8%, 7%, 6%, 5%, 4%, 3%, 2%, 1% or even 0%, i.e. a non-fat product, of the total energy content of said feed, food and/or beverage product.

In some feed, food and/or beverages the natural fat is exchanged with artificial fats, such as olestra also known by its brand name Olean®. In useful embodiments, mucilage and/or one or more active compounds thereof is/are used in combination with an artificial fat and binds the fat-like substances and thus diminishes or abolishes the adverse effect of having such fats in the form of oil and oil-like substances in the colon with accompanying risk of oily leakage, oily spotting etc.

In an interesting embodiment, the feed, food and/or beverage product is ingested in combination with a pharmaceutical product comprising an inhibitor of GI-tract activities and/or an inhibitor of a pancreatic lipase.

It will be understood from the above, that the feed, food and/or beverage product may be consumed together with the mucilage and/or one or more active compounds thereof as two separated parts in a diet, or the mucilage and/or one or more active compounds thereof may be added to the feed, food and/or beverage product and thus become an enriched or fortified feed, food and/or beverage product.

In the examples below, it is shown that when mucilage is incorporated into a baked product the mucilage has an impact on the suppression of hunger and/or the reduction of prospective consumption and/or the reduction of appetite and/or the utilization of the carbohydrates and proteins in the intestinal tract of the subject. A person skilled in the art will easily appreciate that mucilage and/or one or more active compounds thereof, when used in accordance to the invention, will have the same effect when used in other feed, food and/or beverage products. Thus, in useful embodiments, the feed, food and/or beverage product is selected from the group consisting of a cereal, an energy bar, a snack food, a milk product, a baked product, a fruit product, a vegetable product, a meat product, a semi-manufactured product, a ready-to-eat meal, a beverage, and combinations thereof. Examples of specific feed, food and/or beverage products are described below.

The use of mucilage and/or one or more active compounds thereof is in particular useful in milk products due to the natural content of milk calcium which has been shown to have an impact on the faecal excretion of fat. Thus, in milk products fortification with mucilage and/or one or more active compounds thereof, may result in a synergic effect on both excretion of fat and non-fat energy. It will be understood, that it is possible that the same synergic effect may be obtained when other feed, food and/beverage products are fortified with both milk calcium and mucilage.

In preferred embodiments, the feed product is a pet food, including treats and biscuits, selected from the group consisting dog food, cat food, fish feed, bird feed, small animal feed and horse feed.

As will be apparent, preferred features, characteristics and embodiments of one aspect of the present invention may be applicable to other aspects of the present invention.

In line with the above aspects, there is provided a further aspect of the present invention, relating to a method of promoting and/or increasing and/or prolonging the feeling of satiety comprising: identifying a mammal in need for increased and/or prolonged satiety; and providing to said mammal mucilage and/or one or more active compounds thereof. In addition is provided a method of reducing the digestibility of non-fat energy in the intestinal tract of a mammal comprising: a) identifying a mammal in need for a reducing the digestibility of non-fat energy in said mammal's intestinal tract; and b) providing to said mammal mucilage and/or one or more active compounds thereof; wherein said non-fat energy originates from said mucilage and/or one or more active compounds thereof or the food or beverage ingested prior, concomitantly or immediately after said mucilage and/or one or more active compounds thereof.

In accordance with a further aspect of the present invention mucilage and/or one or more active components thereof is provided for use in increasing suppression of hunger and/or increasing reduction of prospective consumption and/or increasing reduction of appetite. The mucilage and/or one or more active components thereof may be used for further promoting and/or increasing and/or prolonging the feeling of satiety.

The present invention further relates to mucilage and/or one or more active components thereof for use as a supplement for ingestion in combination with a pharmaceutical product comprising an inhibitor of GI-tract activities and/or an inhibitor of a pancreatic lipase.

A further aspect of the present of the present invention, relates to mucilage and/or one or more active compounds thereof for use in reducing or decreasing the digestibility of non-fat energy in a mammal. Also, it relates to mucilage and/or one or more active compounds thereof for use in promoting and/or increasing and/or prolonging the feeling of satiety.

As described above, the mucilage and/or one or more active compounds thereof may be used as an ingredient in feed, food or beverage products, or the mucilage and/or one or more active compounds thereof may be used as a dietary supplement. Thus, a useful aspect of the present invention relates to the use of mucilage and/or one or more active compounds thereof as a feed, food and/or beverage ingredient, a dietary supplement or a fortificant for increasing suppression of hunger and/or increasing reduction of prospective consumption and/or increasing reduction of appetite or for reducing the digestibility of non-fat energy in a mammal. In one embodiment, the use of mucilage and/or one or more active compounds thereof is for further promoting and/or increasing and/or prolonging the feeling of satiety in a mammal.

A further aspect relates to the use of mucilage and/or one or more active compounds thereof as a dietary supplement for reducing the digestibility of non-fat energy in a mammal. It further relates to use of mucilage and/or one or more active compounds thereof as a feed, food and/or beverage, fortificant or dietary supplement for promoting and/or increasing and/or prolonging the feeling of satiety in a mammal. In useful embodiments, the dietary supplement may be in the form of a capsule, a pill, a tablet, a chewable tablet, a liquid, or a supplemental bar.

Thus, the present invention also pertains to a method for reducing the digestibility of non-fat energy in a mammal comprising: a) identifying a mammal in need of reducing the digestibility of non-fat energy; and b) providing to said mammal mucilage and/or one or more active compounds thereof as a food ingredient or a dietary supplement. It further pertains to a method of promoting and/or increasing and/or prolonging the feeling of satiety in a mammal comprising: identifying a mammal in need of increased and/or prolonged satiety; and providing to said mammal mucilage and/or one or more active compounds thereof as a food ingredient or a dietary supplement.

It will be understood, that "a mammal in need of reducing the digestibility of non-fat energy" may be a human or a non-human who wishes to reduce its body weight, or a subjects suffering from overweight, such as cosmetic overweight, or obesity as defined above. However, the subject may also be a mammal who wishes to maintain its normal body weight although ingesting food or feed products having high content of high energy. Furthermore, the subject may also be a mammal who wishes to live a healthier life. The subject may furthermore be an individual which periodically has no or limited or inadequate access to food, such as due to occupational and/or recreational activities, including an individual selected from the group consisting of athletes, emergency or rescue workers, military personnel.

In an interesting embodiment, the mucilage and/or one or more active compounds thereof may also be used in combination with pharmaceutical products that work through inhibition in the gastrointestinal tract and pancreatic lipases to inhibit fat degradation and absorption, such as orlistat (tetrahydrolipstatin, formula I),

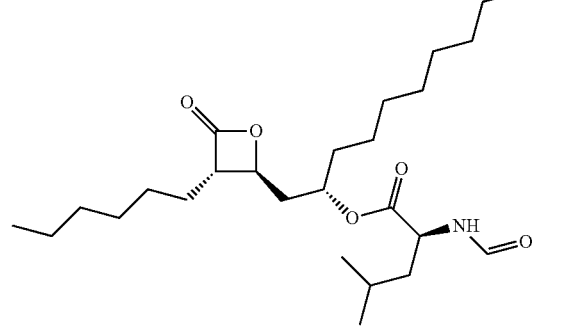

Formula I cetilistsat and other lipase inhibitors. Mucilage and/or one or more active compounds thereof can enhance the weight loss effect of the lipase inhibitors by reducing appetite, and by further energy binding hence increasing the energy excretion. The further advantage of combining mucilage and/or one or more active compounds thereof with pharmaceutical products inhibiting fat degradation and absorption is illustrated by the data in the below Example 3 showing a reduced postprandial response in total plasma triacylglycerol (TAG) as a function of mucilage dose. Thus, an interesting aspect of the present invention relates to mucilage and/or one or more active compounds thereof for use as a supplement or additive for ingestion in combination with a pharmaceutical product comprising an inhibitor of GI-tract activities and/or an inhibitor of a pancreatic lipase.

Mucilage's and/or one or more active compounds thereof capability of increasing suppression of hunger and/or increasing reduction of prospective consumption and/or increasing reduction of appetite and/or increasing promotion and/or prolongation of the feeling of satiety and/or binding the carbohydrates and proteins of concomitantly ingested food is in particular useful in feed, food and/or beverage products having a low content of fat because, as described above, low fat feed and food products tend to contain more carbohydrates compared to feed and food products having a normal/natural fat content. Thus, the incorporation of mucilage and/or one or more active compounds thereof into the feed, food and/or beverage or ingestion of mucilage and/or one or more active compounds thereof as a supplement besides the diet would result in increased suppression of hunger and/or increased reduction of prospective consumption and/or increased reduction of appetite and/or increased promotion and/or prolongation of the feeling of satiety and/or a reduced digestion of these added carbohydrates and proteins.

Accordingly, a further aspect of the present invention relates to a feed, food and/or beverage product having a fat content that provides up to, but not including, 10% of the total energy content of said food and/or beverage product, comprising mucilage and/or one or more active compounds thereof. In useful embodiment, the fat content provides up to 9%, 8%, 7%, 6%, 5%, 4%, 3%, 2%, 1% or even 0%, i.e. a non-fat product, of the total energy content of said feed, food and/or beverage product.

In useful embodiments, the content of mucilage and/or one or more active compounds thereof in the high fat content feed, food and/or beverage product is 1%, 2% 3%, 5%, 10%, 15%, 20%, 30%, 40% or 50% by weight of the feed, food and/or beverage product. In useful embodiments, the total content of a mucilage and/or one or more active compounds thereof, when used according to the invention in the feed, food and/or beverage product typically corresponds to a content of 1 to 50%, including 5 to 40%, such as 10 to 30%, including 15-25% by weight of the feed, food and/or beverage product.

In preferred embodiments, the feed, food and/or beverage product is selected from the group consisting of a cereal, a snack food, a milk product, a baked product, a fruit product, a vegetable product, a meat product, a semi-manufactured product, a ready-to-eat meal and combinations thereof.

In useful embodiments, the snack food is selected from the group consisting of energy bar, Banana chips, Bugles, Cheese curls, Cheese puffs, Combos, Corn chips, Nachos, Pita chips, Pretzel, Potato chips, Pork rind, Tortilla chips, candy bars, jelly beans, gummy bears, liquorice, lollipops, gumdrops, hard candy, taffy, jerky, mixed nuts, popcorn and combinations thereof.

In preferred embodiments, the feed, food and/or beverage product is a fruit product selected from the group consisting of a fruit sauce, marmalade, fruit snack and combinations thereof.

In preferred embodiments, the feed, food and/or beverage product is a vegetable product is selected from the group consisting of French fries, onion rings, baked beans and combinations thereof.

Examples of the semi-manufactured and a ready-to-eat meal product include noodles and pizza, respectively.

Useful examples of beverages include a soft drink, carbonated water, a fruit juice, non-carbonated sports drink, a beverage comprising carbonated water or combinations thereof.

In preferred embodiments, the feed, food and/or beverage product is a milk product selected from the group consisting of butter, cream, butter milk, fermented milk such as yoghurt, junket, quark, fromage frais or sour milk, drinking chocolate/chocolate milk, flavoured milk drink, milkshake, ice cream, cheese and combinations thereof.

In further embodiments, the feed, food and/or beverage product is a baked product which is selected from the group consisting of bread, rye bread, cookies, biscuit, tea-biscuit, cracker, pie-crust, pâté, patty, doughnuts and combinations thereof.

In useful embodiment, the feed, food and/or beverage product is a meat product selected from the group consisting of liver paste, sausages, meatballs, beef burger, fish cake and combinations thereof.

Examples of useful pet foods, including treats and biscuits for pets, may be selected from the group consisting dog food, cat food, fish food, small animal food, horse food, bird food, farm animal food and combinations thereof.

In interesting embodiment, the feed, food and/or beverage product is one wherein the use of mucilage results in an excess excretion of non-fat energy in the range of from 1 to 20 kJ/day/g mucilage, such as in the range of from 5 to 15 kJ/day/g mucilage, such as in the range of from 10 to 15 kJ/day/g mucilage.

In further interesting embodiments, the feed, food and/or beverage product is one wherein the mucilage is characterised by having a negative partial digestible non-fat energy value ranging from −1 to −20 kJ/g of mucilage, including a negative partial digestible non-fat energy value in the range of from −5 to −15 kJ/g, such as in the range of from −10 to −15 kJ/g of mucilage.

The feed, food and/or beverage product according to the invention may have a content of mucilage and/or one or more active compounds thereof which is in the range of 1-80 g/10 MJ. According to preferred embodiments of the invention, the content of mucilage and/or one or more active compounds thereof may be within the range of 1-30 g/10 MJ, 1-40 g/10 MJ, 1-50 g/10 MJ, 1-60 g/10 MJ, 1-70 g/10 MJ, 10-35 g/10 MJ, 10-45 g/10 MJ, 10-55 g/10 MJ, 10-65 g/10 MJ, 10-75 g/10 MJ, 40-80 g/10 MJ, 50-80 g/10 MJ, 60-80 g/10 MJ, or such as 70-80 g/10 MJ.

As mentioned above, mucilage and/or one or more active compounds of the mucilage may be useful in feed, food and/or beverage products, where the natural fat is substituted with an artificial fat and where thus the content of carbohydrates and protein is increased in order to compensate for the natural taste and/or structure of the natural fat. Accordingly, in an interesting aspect of the present invention, a feed, food and/or beverage product comprising mucilage and/or one or more active compounds thereof and an artificial fat is provided. It is contemplated that in such a product, the mucilage or the active compound thereof will bind to the carbohydrates and the proteins and simultaneously to the artificial or fat-like substances (e.g. olestra) in the gastrointestinal tract, and thus diminish or abolish the adverse effect of having fats in the form of oil and oil-like substances in the colon.

In one interesting aspect of the present invention, the mucilage and/or one or more active compounds thereof is used to increased suppression of hunger and/or increased reduction of prospective consumption and/or increased reduction of appetite and/or increased promotion and/or prolongation of the feeling of satiety and/or reduce the digestibility of carbohydrates and proteins in feed, food and/or beverage not containing any fat. For example, instead of exchanging the sugar in diet products, mucilage may be used to secure that not all of the carbohydrates in such a product are digested. Thus, the present invention also pertains to a non-fat feed, food and/or beverage product comprising mucilage or flax seed mucilage and/or one or more active compounds thereof.

In the present context, the term "non-fat feed, food and/or beverage products" relates to products containing no fat, i.e. 0%, or in a preferred embodiment at the most 1%.

Examples of non-fat feed, food and/or beverage product include a soft drink, carbonated water, a fruit juice, non-carbonated sports drink, a beverage comprising carbonated water, jelly beans, gummy bears, liquorice, lollipops, gumdrops, hard candy, fruit sauce and combinations thereof.

The non-fat feed, food and/or beverage product may also be a pet food (including treats and biscuits) selected from the group consisting dog food, cat food, fish feed, bird feed, small animal feed and horse feed.

In preferred embodiment, the non-fat feed, food and/or beverage product is one wherein the mucilage is characterised by having a negative partial digestible non-fat energy value ranging from −1 to −20 kJ/g of mucilage.

In a further aspect, the present invention provides a method for preparing a feed, food and/or beverage product for reducing the digestibility of non-fat energy in the intestinal tract in a mammal comprising formulating mucilage and/or one or more active compounds thereof into the feed, food and/or beverage product. It also provides a method of making a composition for promoting and/or increasing and/or prolonging the feeling of satiety, comprising: providing mucilage and/or one or more active compounds thereof; and formulating said mucilage and/or one or more active compounds thereof to a weight-loss composition.

It should be understood that any embodiments and/or feature discussed above in connection with the methods and uses of a mucilage and/or one or more active compounds thereof according to the invention apply by analogy to the below aspects of the present invention.

It follows from the above, that the mucilage and/or one or more active compounds thereof reduces the digestibility of non-fat energy in the gastrointestinal tract. Hence, useful applications include use of mucilage and/or one or more active compounds thereof for prevention or treatment of medical overweight or obesity and their comorbidities such as the metabolic syndrome, type 2 diabetes, hyperlipidemia, and cardiovascular diseases. Furthermore, useful applications of mucilage and/or one or more active compounds thereof include methods for preparing weight loss compositions, dietary supplements and pharmaceutical composition comprising mucilage and/or one or more active compounds thereof for reducing the digestibility of non-fat energy or for increasing faecal non-fat energy excretion in a mammal.

In preferred embodiments of the below aspects, the mucilage or the active compound thereof originates from flaxseed.

The below methods with regard to prevention or treatment of medical overweight and obesity, are preferably directed to a subject such as a human, but any mammal, such as a non-human may also be treated with the mucilage and/or one or more active compounds thereof. Examples of preferred subjects that will benefit from this use of mucilage and/or one or more active compounds thereof are outlined in the above Table 1. It is evident that subjects with a BMI above 18.5 and in particular above 25 will benefit of the use of mucilage.

The typical dose of mucilage which may be used in the below methods for reducing the digestibility of non-fat energy and thus for the prevention or treatment of medical overweight or obesity is equivalent to about 1 to 45 g mucilage/day resulting in a loss of faecal non-fat energy from the normal 4 to 10% of ingested non-fat energy to 15-25%. This corresponds to an additional loss of faecal non-fat energy of 375-750 kJ/day, or 300-600 g body weight per month.

Accordingly, in an aspect, the present invention relates to the use of mucilage and/or one or more active compounds thereof for the preparation of a composition, wherein the composition is formulated for oral administration of an effective amount of said mucilage and/or one or more active compounds thereof for the treatment or prevention of medical overweight or obesity. In a useful embodiment the composition is for use or ingestion in combination with a pharmaceutical product comprising an inhibitor of GI-tract activities and/or an inhibitor of a pancreatic lipase.

One further aspect provides the use of mucilage and/or one or more active compounds thereof for the preparation of a composition, wherein the composition is formulated for oral administration of an effective amount of said mucilage and/or one or more active compounds thereof for promoting and/or increasing and/or prolonging the feeling of satiety. In a useful embodiment the composition is for use or ingestion in combination with a pharmaceutical product comprising an inhibitor of GI-tract activities and/or an inhibitor of a pancreatic lipase.

In the same line, another aspect pertains to a method of preventing, reducing treating overweight or obesity comprising a) identifying a subject with overweight and obesity; and b) providing to said subject an effective amount of a composition comprising mucilage and/or one or more active compounds thereof. It also provides a method of promoting and/or increasing and/or prolonging the feeling of satiety, comprising identifying a person with overweight and/or obesity; and providing to said person an effective amount of a composition comprising mucilage and/or one or more active compounds thereof.

The above composition may be a pharmaceutical composition, or the composition may be a feed, food and/or beverage product selected from the group consisting of cereal, an energy bar, a snack food, a milk product, a baked product, a fruit product, a vegetable product, a meat product, a semi-manufactured product, a ready-to-eat meal, a beverage, and combinations thereof. Examples of specific feed, food and/or beverage product are described above. In a preferred embodiment, said feed, food and/or beverage product has a fat content that provides up to, but not including, 10% of the total energy content of said feed, food and/or beverage product.

In an interesting embodiment of the above aspects, the composition is for use or ingestion in combination with a pharmaceutical product comprising an inhibitor of GI-tract activities and/or an inhibitor of a pancreatic lipase. Mucilage and/or one or more active compounds thereof can thus be used in combination with pharmaceutical products that work through inhibition in GI-tract and pancreatic lipases to inhibit fat degradation and absorption, such as orlistat, cetilistsat and other lipase inhibitors. Mucilage and/or one or more active compounds thereof can enhance the weight loss effect of the lipase inhibitors by reducing appetite, and by further fat binding hence increasing the fecal fat excretion. In addition, mucilage and/or one or more active compounds thereof can bind the unabsorbed fat so it does not reach the colon in a liquid form (i.e. instead bound to mucilage and/or one or more active compounds thereof), and therefore reduce or elimination the adverse GI effects of lipase inhibitors, and non-absorbable fat substitutes such as olestra.

A further aspect relates to mucilage and/or one or more active compounds thereof for use in treatment or prevention of medical overweight or obesity. It also relates to mucilage and/or one or more active compounds thereof for use in promoting and/or increasing and/or prolonging the feeling of satiety. Furthermore, the invention provides mucilage and/or one or more active compounds thereof as a medicament.

The present invention also relates to a method to inhibit weight gain, which comprises: a) identifying a person in need of an inhibition of weight gain; and b) providing to said person an effective amount of mucilage and/or one or more active compounds thereof.

Furthermore, the present invention provides a method of making a weight-loss composition comprising: a) providing mucilage and/or one or more active compounds thereof; and b) formulating said mucilage and/or one or more active compounds thereof to a weight-loss composition.

A further aspect of the present invention relates to a pharmaceutical composition comprising mucilage and/or one or more active compounds thereof as an active principal and a pharmaceutically acceptable carrier, a vehicle and/or a diluent. Preferably, the composition is formulated for oral administration.

In a useful embodiment, the pharmaceutical composition is one wherein the active principal is orlistat.

In preferred embodiment, and based on the results described below, the pharmaceutical composition is characterized in that it contains from 1 to 45 g of mucilage. In further embodiments, the composition contains 1 to 40 g mucilage, including 10 to 35 g of mucilage. Typically, the pharmaceutical composition contains about 5 g of mucilage, such as 10 g, 15 g, 20 g, 25 g, 30 g, or 35 g grams of mucilage.

The capability of mucilage and/or one or more active compounds thereof of reducing the digestibility of non-fat energy in the gastrointestinal tract may also be utilised in the prevention and treatment of cosmetic overweight, and for preparing cosmetic compositions and dietary supplements useful for prevention and treatment cosmetic overweight.

In preferred embodiments of the below aspects, the mucilage or the active compound thereof originates from flax seed.

The below methods with regard to prevention and treatment of cosmetic overweight are preferably directed to a subject such as a human, but any mammal, such as a non-human may also be treated with the mucilage and/or one or more active compounds thereof. Examples of preferred subjects that will benefit from this use of mucilage and/or one or more active compounds thereof are subjects having a weight that does not have any immediately medical implications on the individual but may be in a range that is not satisfactory for cosmetic reasons. As fashion with respect to body size changes some individuals may interpret the "normal weight" as "cosmetic overweight". As a consequence such individuals may have a desire of treating cosmetic overweight.

The typical dose of mucilage which may be used in the below methods for reducing the digestibility of non-fat energy and thus for the prevention or treatment of cosmetic overweight or obesity is equivalent to about 1 to 45 g mucilage/day resulting in a loss of faecal non-fat energy from the normal 4 to 10% of ingested non-fat energy to 15-25%. This corresponds to an additional loss of faecal non-fat energy of 375-750 kJ/day, or 300-600 g body weight per month.

Accordingly, a further aspect of the present invention relates to a method for the cosmetic treatment or prevention of overweight, which comprises orally administering an effective amount of mucilage and/or one or more active compounds thereof or a composition comprising mucilage and/or one or more active compounds thereof.

In the same line, a still further aspect relates to the use of mucilage and/or one or more active compounds thereof for the preparation of a composition, wherein the composition is formulated for oral administration of an effective amount of said mucilage and/or one or more active compounds thereof, for the treatment or prevention of cosmetic overweight. In a useful embodiment, the composition is formulated as a feed, food and/or beverage product comprising mucilage and/or one or more active compounds thereof.

In a useful embodiment of the above aspects, the composition is a cosmetic composition, preferably, formulated for oral administration.

In preferred embodiments, the method is one wherein the composition comprising mucilage and/or one or more active compounds thereof is a feed, food or beverage selected from the group consisting of a cereal, an energy bar, a snack food, a milk product, a baked product, a fruit product, a vegetable product, a meat product, a semi-manufactured product, a ready-to-eat meal, a beverage, and combinations thereof. In an interesting embodiment, the feed, food and/or beverage product has a fat content that provides up to, but not including, 10% of the total energy content of said food and/or beverage product.

In one embodiment, the feed, food or beverage product is for use or ingestion in combination with a pharmaceutical product comprising an inhibitor of GI-tract activities and/or an inhibitor of a pancreatic lipase.

Further aspects of the present invention relates to mucilage and/or one or more active compounds thereof for use in treatment of cosmetic overweight, and to a cosmetic composition comprising mucilage and/or one or more active compounds thereof. In a preferred embodiment, the cosmetic composition is one which contains from 1 to 45 g of mucilage. In further embodiments, the composition contains 1 to 40 g mucilage, including 10-35 g of mucilage. Typically, the cosmetic composition contains about 5 g of mucilage, such as 10 g, 15 g, 20 g, 25 g, 30 g, or 35 g grams of mucilage.

An interesting aspect of the invention relates to a method of improving, facilitating or maintaining the bodily appearance of a mammal having a normal weight, comprising a) orally administering to said mammal mucilage and/or one or more active compounds thereof in a dosage effective to increase faecal excretion of non-fat energy; b) and repeating said dosage until a cosmetically beneficial loss of body weight has occurred.

A further aspect relates to a method of extraction of mucilage from flaxseed. A skilled person will be aware of appropriate methods for fractionation of flaxseed components such as mucilage and/or one or more active compound thereof.

In one embodiment, the method comprises the step of a) heating the flaxseeds for 2-3 h, such as 4-5 h, at a temperature around 90° C. in a water extraction procedure, b) separating the extract from the seeds by sieving (e.g. using a 40 mesh), and c) drying the obtained product by freeze drying or spray drying.

An even further aspect relates to a method of purification of mucilage and/or one or more active compound thereof.

A last aspect of the present invention relates to purified mucilage and/or one or more active compounds thereof. In a preferred embodiment, purified mucilage and/or one or more active compounds thereof is/are one wherein the content of fat, carbohydrates and/or protein is reduced compared to non purified mucilage and/or one or more active compounds thereof.

The following examples are included to demonstrate particular embodiments of the invention. However, those of skill in the art should, in view of the present disclosure, appreciate that many changes can be made in the specific embodiments which are disclosed and still obtain a like or similar result without departing from the spirit and scope of the invention. The following examples are offered by way of illustration and are not intended to limit the invention in any way. The invention will now be described in further details in the following non-limiting examples and figure, wherein

EXAMPLES

Example 1

Rat Feeding Trial 1.1 Materials and Methods

Sixty male Wistar rats (200 g) were allocated to one of five different dietary treatments (A-E) (n=10/group). The rats were fed the experimental diets for a total period of 21 days, of which the last 5 days they were housed in metabolic cages during a balance period. Faeces and urine was collected during the 5 d balance period and on days 1, 15 and 22, the rats were weighed. The rats were provided with 25 g feed/d (ad libitum) and food and water consumption was measured.

All diets were prepared to be equal in macronutrient composition, with 11% protein, 20% fat but differing in fibre content: group A (control) received no added fibres, groups B to D received 5% fibres in the diet from different sources (whole flaxseed, ground flaxseed or flaxseed mucilage, respectively) and group E received 10% fibres from flaxseed mucilage. Faecal samples were analysed for total fat and energy content (Table 1.1).

1.2 Results

After 21 days on an one of six ad libitum diets, there were significant difference between the diets (p=0.013), where diet E resulted in significant lower body weight gain compared to all other diets after adjusting for initial body weight (Table 1.2).

TABLE 1.1

Faecal samples analysed for total fat and energy content

| Diet group | Feces excreted (g/d) | Fecal fat excretion (mg/d) | Fecal energy excretion (kcal/d) | Fecal non-fat energy excretion (kcal/d)[#] |
|---|---|---|---|---|
| A-control | 0.94[a] | 113[a] | 1.91[a] | 0.91 |
| B-whole | 3.46[b] | 271[a] | 7.94[b] | 5.54 |
| C-ground | 3.33[bc] | 303[a] | 8.24[b] | 5.56 |
| D-5musil | 4.64[c] | 264[a] | 9.16[b] | 6.82 |
| E-10musil | 7.22[d] | 719[c] | 16.69[c] | 10.33 |

[#]Calculations based on mean values, thus no statistical analysis performed

TABLE 1.2

Body weight development of rats fed a high fat diet differing in fibre content (n = 10).

| Diet group | Final body weight (g) | Body weight gain (g) | Weight gain as % of initial body weight[#] |
|---|---|---|---|
| A-control | 287.79[a] | 88.82[a] | 31.0 |
| B-whole | 290.60[a] | 91.75[a] | 31.6 |
| C-ground | 282.84[a] | 85.41[a] | 29.8 |
| D-5muc | 285.04[a] | 86.87[a] | 30.3 |
| E-10muc | 259.75[b] | 60.68[b] | 23.5 |
| U-untreated | 197.49* | — | — |

*Not included in statistical analysis
[#]Calculations based on mean values, thus no statistical analysis performed The amount of faeces excreted was clearly affected by an increased intake of fibres ranging from 0.94 g/d when given a control diet to 7.22 g/d. The increase in faecal matter is a result of both an increase in faecal water content (increased from app. 35% to 50%) and dry matter content (increased from app. 0.6 g/g to 3.5 g/d. There was no difference in feed or fat intake (g/d) between the rats on the different diets (p=0.32). Also, the dry matter content of the feed mixtures only varied little between the diets, ranging from 97.29 to 97.97%. We observed that differences in fibre content of the diets have not resulted in adaptation in terms of changes in absolute amounts of feed intake. Thus, the differences observed in faecal excretion patterns can only be ascribed to the composition of the feed mixtures (Table 1.3).

The digestibility of energy was significantly affected by the differences in fibre content, in that group E, which was fed 10% of fibres from flaxseed mucilage, reduced the energy digestibility by app. 20% compared to the control group. When considering energy derived from non-fat sources, i.e. carbohydrates and protein, a similar pattern in reduction of the energy utilization is observed. Thus, although these fibres have been shown to have a high affinity to lipids, other nutritive components are affects by the addition of fibres to the diet.

TABLE 1.3

Feed intake and calculated energy digestibility after a 4d balance period in rats fed a high fat diet differing in fibre content (n = 9-10).

| Diet group | Feed intake (g/d) | Total energy intake (kcal/d) | Non-fat energy intake (kcal/d) | Total energy digestibility (% of intake) | Fat digestibility (% of intake) | Non-fat energy digestibility (% of intake) |
|---|---|---|---|---|---|---|
| A-control | 14.25[a] | 73.07[a] | 46.73[a] | 96.98[a] | 95.92[a] | 98.05[a] |
| B-whole | 15.56[a] | 79.16[a] | 50.61[a] | 90.12[b] | 91.73[b] | 89.05[b] |
| C-ground | 15.45[a] | 77.74[a] | 49.72[a] | 89.52[b] | 90.54[b] | 88.80[b] |
| D-5musil | 14.88[a] | 75.21[a] | 47.19[a] | 88.02[b] | 91.87[b] | 85.53[b] |
| E-10musil | 14.08[a] | 70.44[a] | 45.43[a] | 77.28[c] | 74.98[d] | 77.25[c] |

1.3 Discussion and Conclusion

Feeding 10% flaxseed mucilage to growing rats has significant effects on weight development. This effect is believed to be due to the inhibition of nutrient uptake in the small intestine facilitated by the dietary fibres, which is supported by the reduced energy digestibility. Also, there is an effect of 5% fibres from flaxseed sources on energy digestibility, and thus a dose-response relationship exists. The pattern seen in the effects on energy digestibility is repeated when looking exclusively at non-fat energy digestibility. However, all the groups fed 5% of fibres from different flaxseed sources no longer show very similar responses, as there a is a tendency towards a more pronounced effect on non-fat energy from fibres from flaxseed mucilage than fibres from whole or ground flaxseeds (p=0.15). It should be noted that all the diets contained equal amounts of fat, thus this observation is not due to differences in fat intake. In conclusion, the flaxseed mucilage has strong effects on nutrient utilisation which can be exploited in foods aimed at reducing not energy intake but uptake of human foods whether these foods are high or low in fats.

Example 2

Human Intervention Study
2.1 Materials and Methods

In a randomized cross-over study, gross intake and faecal excretion of total and non-fat energy was measured in 11 young healthy men aged 24.6±2.7 y. During each 7 days intervention period, the subjects received a basal diet plus 300 g either ordinary rye bread or rye bread containing 6 g flaxseeds/100 g. This is equivalent to an increase in daily fibre intake from flaxseed of 5 g. Faecal samples were collected on the morning on the 7th day of the intervention, and the daily excretion of faecal weight and energy was corrected to a theoretical daily output of transit markers which was given to the subjects on day 4, 5 and 6 (60/d).
2.2 Results Addition of flaxseeds to breads increased daily gross intake of energy from 14.7 MJ/d to 15.0 MJ/d (p<0.001). The amounts of apparently digested energy (kJ/d) was lowered when subjects consumed the flaxseed rye bread (p<0.001), and the energy digestibility was decreased from 91.7 to 87.3% of intake. However, when the amount of energy derived from non-fat sources was considered which has not been done previously, the excretion of energy from non-fat sources increased from 880 kJ/d to 1080 kJ/d. In subjects consuming flaxseed rye bread, the non-fat energy intake was 10893 kj/d and in the control group the non-fat energy intake was 10852 kj/d. When related to the intake of non-fat energy, the change in excretion of non-fat energy corresponded to a decreased digestibility of app. 2%.
2.3 Discussion and Conclusion Enrichment of bread with whole flaxseeds does not appear to result in increased energy intake when added to breads, but the results rather indicate an impairment of nutrient utilisation. If half of the daily recommended intake of dietary fibres (15 g) was provided in the form of flaxseed mucilage (app. 30 g), an excess excretion of non-fat energy of up to 600 kJ/d could be expected if the results obtained here are extrapolated. Thus, a daily dose of flaxseed mucilage of app. 30 g represents an efficient strategy to prevent energy over-consumption and weight gain.

Considering the promising results obtained in rats on the extracted mucilage fraction, it is expected that the same effects seen when whole flaxseeds in rye breads can be obtained using a daily dose of flaxseed mucilage.

Example 3

Human Test Meal Study
3.1 Materials and Methods
Study Design

Four different iso-caloric meals were tested in the 18 subjects according to a double-blinded randomized multiple crossover design. The subjects were randomly assigned to the sequence of the test meals and there was a wash out period of minimum 3 weeks between the four test meal days. Prior to each of the four meal test days the study subjects were instructed to follow a standardized fasting procedure which included abstention from alcohol and high-fat products such as potato crisps, high fat dairy products, and chocolate for 48 hours as well as abstention from hard physical activity for 24 hours prior tot the test meal. On the evening before the meal test they consumed a standardized low-fat evening meal no later than 8 pm providing 4.5 MJ consisting of a pasta dish, fruit juice and biscuits (22 E % from fat, 18 E % from protein and 60 E % from carbohydrates), which was prepared at the department. Furthermore, they were only allowed 500 mL of water between 8 pm and the time of the test meal on the following day.

On the meal test day, the subjects arrived at the Department of Human Nutrition by car, bus, train or slow walk and were weighed upon arrival wearing only underwear. Weight was measured in kg to the nearest 0.1 kg. A venflon catheter was inserted in the antecubital arm vein and after 10 minutes rest, a fasting blood sample was drawn, Hb concentration>8 mmol/l verified, and the subjects' appetite sensation was assessed (time point 0). Hereafter the test meal was served, for which the subjects' were allowed a maximum of 20 minutes to consume. Palatability of the test meal was then assessed. Blood samples were continuously drawn (time points 30, 60, 90, 120, 180, 240, 300, and 420 min) and appetite sensation was assessed every half hour (time points 30 to 420). At time points 120 and 240 minutes, 250 ml of water was served and they were instructed to drink it within 10 minutes. Apart from the two servings of water, the subjects were not allowed any foods or drinks throughout the day. During the day the subjects were allowed to read, watch television or video, listen to the radio or use their computer. The subjects were allowed to talk to each other as long as the 10 conversation did not involve food, appetite or related subjects. After the last blood sample was drawn 420 minutes after the test meal was served, an ad libitum meal consisting of pizza slices with tomato sauce, ham and cheese (1,060 kJ/100g) and 500 ml water was served. Food and water intake was registered and energy intake calculated. The amount of water that the subjects drank on the first meal test was repeated at all four meal tests.

Test Meals

The four test meals were given as high-fat breakfast meals which provided app. 40% of the subjects' daily energy requirements estimated using an equation taking into account the body weight, gender, age and physical activity level estimated at recruitment (4 or 5 MJ). The four test meals each provided 48 g of fat per 5 MJ and cholesterol content was less than 100 mg in all test meals. Energy distribution of the test meals did not differ (15 E % from protein, 36 E % from fat, and 49 E % from carbohydrates). Macro- and micronutrient composition of the test meals was estimated using Dankost 3000 dietary assessment software (Danish Catering Center, Herlev, Denmark). The test meals were prepared at the Department of Human Nutrition and consisted of two buns with cheese, butter, ham and 400 ml of water, and the different flaxseed fractions were baked into the buns. Fiber content and source differed between then meals:

| | |
|---|---|
| Control (C) | 0 g/5 MJ |
| Whole flaxseed (WF) | 5 g/5 MJ from addition of whole flaxseeds |
| Low dose of flax mucilage (LM) | 5 g/5 MJ from addition of flax mucilage |
| High dose mucilage (HM) | 10 g/5 MJ from addition of flax mucilage |

Fiber content of the flaxseed mucilage was measured according to the AOAC method and used to calculate the content of flaxseed mucilage in the LM and HM meals. A table value on fiber content in flaxseeds was used to calculate the content of whole flaxseeds in the WF meal.

Subjective Appetite Sensation and Meal Palatability

To assess appetite sensation visual analogue scales (VAS) were used. They are 100 mm in length with words anchored at each end, expressing the most positive and the most negative rating, were used to assess hunger, satiety, fullness, thirst, prospective food consumption, desire to eat something fatty, salty, sweet or savory plus well-being, and the palatability (five questions) of the test meal (not shown). The questionnaires were made as small booklets showing only one question at a time. Subjects were not allowed to discuss or compare their ratings with each other and could not refer to their previous ratings when filling in the VAS booklets. The test meals and ad libitum meals were assessed in terms of physical appearance, smell, taste, off taste and overall pleasantness using VAS.

Serum Concentrations of TAG, Total, HDL-, and LDL-Cholesterol and Insulin

Serum concentrations of TAG and total cholesterol (TC) was assessed using colorimetric test kits (Roche TG, Roche Diagnostics GmbH, Mannheim, Germany), The intra-assay variations were 0.6% and 0.9%, respectively. HDL-cholesterol (HDL-C) and LDL-C were measured in serum using a homogeneous enzymatic colorimetric test kits (Roche HDL-C plus $2^{nd}$ generation and LDL-C plus $2^{nd}$ generation, Roche Diagnostics GmbH, Mannheim, Germany). Both intra-assay precisions were 1.8%. All lipid analyses were performed on a COBAS MIRA Plus (Roche Diagnostic Systems Inc., Mannheim, Germany). Serum insulin was measured by solid-phase, 2-site chemiluminescent immunometric assay (Immulite/immuliter 1000 insulin; Diagnostic Products Corporation, Los Angeles, Calif.) with the use of an Immulite 1000 analyzer (Diagnostic Products Corporation). The intraassay and interassay CVs were 2.5% and 4.9%, respectively.

Chylomicron Concentrations of TAG

Chylomicron TAG was quantified by $^1H$ NMR spectroscopy validated against ultracentrifugation, which is considered the gold standard method for chylomicron isolation. For this purpose, a total of 160 samples were measured using both measurements, and these were used to make a regression model for prediction of CM TAG content from NMR spectra obtained from the remaining samples (Savaroni et al., unpublished). The reported values are based on the ultracentrifugation method for the 160 samples and on the H NMR spectroscopy method for the remaining samples but are considered as one dataset in the statistical.

Ultracentrifugation: Chylomicron fractions were isolated as described elsewhere (25) by careful over-laying 3 ml of plasma with 2.5 ml salt solution of density 1.006 kg/l. The ultracentrifugation tubes were centrifuged for 23 minutes at 30,000 rpm (L7-55, Beckmann Instruments, Palo Alto, Calif.) using a fixed angle rotor (50.4 Ti, Beckmann Instruments). The tubes were sliced 45 mm from the bottom, and the TAG concentration was measured in the chylomicron (top) and bottom fractions as well as in a plasma sample by a colorimetric test kits (Roche TG, Roche Diagnostics GmbH, Mannheim, Germany). Intra- and inter-assay precisions were 0.6% and 1.4%, respectively.

H NMR spectroscopy: $^1$H NMR spectra were acquired at 37° C. on a Bruker Avance 500 spectrometer operating at a Larmor frequency of 500.13 MHz for $^1$H using a 120 µl flow-probe. A pulse sequence using presaturation followed by a composite pulse was used to obtain optimum water suppression. All spectra were acquired employing a spectral width of 10417 Hz, an acquisition time of 1.57 s, a relaxation delay of 5 s and 64 scans. A calibration using PLS modeling using the entire spectral information to develop the PLS model yielded a resulting correlation coefficient, $r^2$, of 0.90 and a root-mean-square-error-of-cross-validation (RMSECV) of 0.174 mg/g TAG using just 3 principal components. In this extension to PLS the NMR spectra are divided up into a number of small regions or intervals for each of which a local PLS regression model is calculated. Evidently only two spectral regions are able to improve the regression model, when compared to the global regression model: one region which include the vicinal methylene groups to the estergroups of the TAGs and one region which includes the (poly)-methylene protons at centered at 1.28 ppm. The latter region give rise to the best and most parsimonious model for predicting the chylomicron TAGs with a correlation coefficient, $r^2$, of 0.92 and a RMSECV of 0.156 mg/g TAG using only 3 principal components.

Plasma Concentrations Of Glucose, Ghrelin And Glugacon-Like Peptide-1

Plasma glucose was determined spectrophotometrically at 340 nm (COBAS MIRA Plus, Roche Diagnostics System Basel, Switzerland). Ghrelin concentrations in plasma were measured by radioimmunoassay with an antiserum Plasma ghrelin concentrations were determined by using a radioimmunoassay kit (catalog no. GHRT-89k; Linco Research, St Charles, Mo.) that measures total ghrelin. GLP-1 concentrations in plasma were measured by radioimmunoassay after extraction of plasma with 70% ethanol (by vol, final concentration). Carboxy-terminal GLP-1 immunoreactivity was determined by using antiserum code no. 89390, which has an absolute requirement for the intact amidated carboxy-terminus of GLP-1 7-36 amide and cross-reacts <0.01% with carboxy-terminally truncated fragments, and 89% with GLP-1 9-36 amide, the primary metabolite of dipeptidyl-peptidase IV-mediated degradation. The sum of the 2 components (total GLP-1 concentration) reflects the rate of secretion of the L cell.

Statistical Power, Calculations And Statistical Analyses

Eighteen subjects were recruited for the study in order to obtain a power of 0.8 when looking for an effect size of 10% on VAS. Flint et al (27) have studied the reproducibility, power and validity of VAS and they found that using a paired design, when looking for an effect size of 10%, 18 subjects are needed to achieve sufficient study power and thereby minimising the risk of a type II error ('false-negative' result).

The area under the curve (AUC) was calculated for all variables as the total increase above zero. AUC for CM TAG was calculated. For TAG and CM TAG, data from one subject was removed due to abnormal concentrations on two of the four meal tests. Due to analytical problems, some values were missing for CM TAG. Three baseline concentrations were estimated as a mean of the three baseline levels for the other meal test days, and another twenty-seven concentrations were estimated as a mean between the time points before and after on the same meal test day. The remaining 21 values remain missing as no estimates could be given resulting in an unbalanced analysis for CM TAG.

All statistical analyses and calculations were performed using the Statistical Analysis System software package, version 9.1 (SAS Institute inc., Cary, N.C.). All dependent variables were controlled for homogeneity of variance investigation and normal distribution by investigation of residual plots, normal probability plots and histograms. If the distribution of a variable was skewed it was log-transformed prior to analyses, and back-transformed before presentation. A repeated measures ANCOVA analysis was used to examine the effect of meal and time on the postprandial response. This was performed in PROC MIXED, where subject was modeled as a random variable and corresponding baseline value and body weight were modeled as covariates. Subject*period was used to model the covariance structure (Spatial Gaussian), and period was included as systematic variable. ANCOVA was used to examine the effect of meal on AUCs. This was performed in PROC MIXED, where subject was modeled as a random variable and the baseline values and body weight were modeled as covariates, and period included as a class variable. Posthoc pairwise comparisons were made using Tukey-Kramers adjustment for meal or for meal*time, when significant. All data are presented as means±SEM unless otherwise stated and the statistical significance level is defined as $p<0.05$.

3.2 Results

Figure 2:
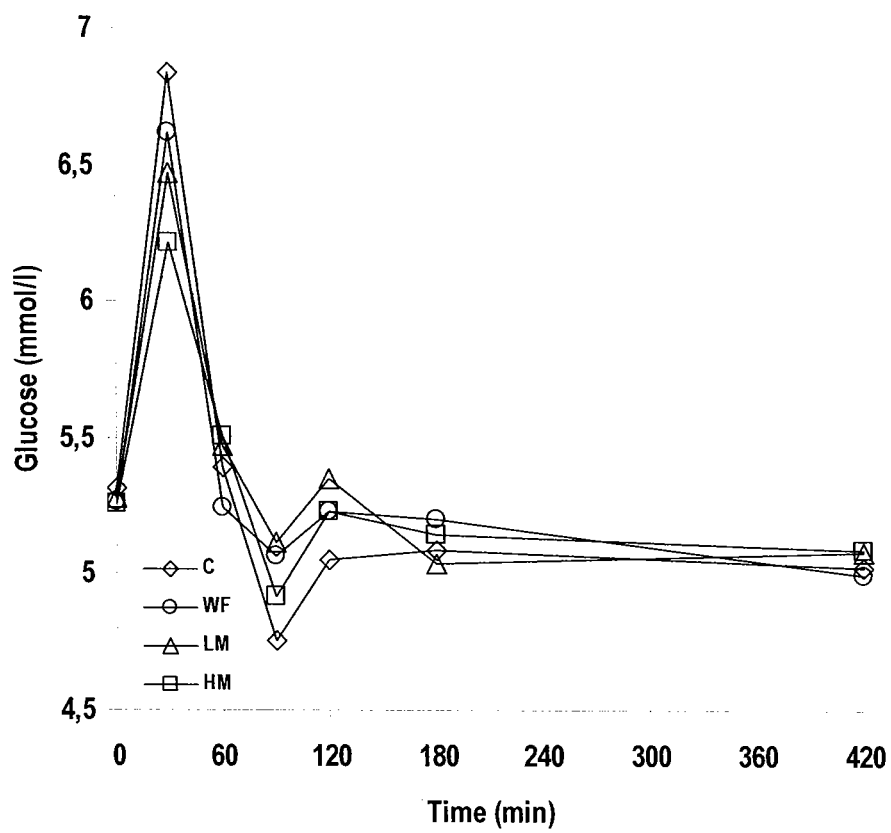
FIGS. 2-4 show mean glucose (FIG. 2), insulin (FIG. 3), lactate and free fatty acids (FFA) (FIG. 4) during the 7 hours after 4 iso-caloric test meals (C: control; WF: whole flaxseeds; LM: low dose flaxseed mucilage; HM: high dose flaxseed mucilage) and corresponding AUCs (least square means ±SEM) (n=18). Repeated measures ANCOVA (adjusted for baseline, body weight and period) showed a strong effect of time on glucose, but no overall effect of meal. A strong time*meal interaction was observed for insulin ($p<0.01$). Posthoc pairwise comparisons that the HM meal resulted in lower insulin concentrations compared to meal WF and mean meal C after 30minutes ($p<0.01$) and compared to meal WF at 180 minutes ($p=0.027$); and higher at 420 minutes compared to meal WF ($p<0.01$) and meal C ($p=0.027$). Meal LM gave lower insulin response compared to meal WF at 30 minutes ($p=0.026$). A strong time*meal interaction was observed for FFA ($p<0.01$) and posthoc pairwise comparisons showed meal HM to be lower compared to meal WF at 420 minutes ($p=0.013$). ANCOVA (adjusted for baseline, body weight and period) showed no effect of meal on AUC for glucose. AUC for insulin to be lower for meal LM compared to meal C ($p=0.034$) and WF (0.028) and lower for meal HM compared to meal C and WF ($p<0.01$). AUC for FFA was affected by meal ($p=0.01$). Posthoc comparisons showed that AUC for meal HM was lower compared to meal WF ($p<0.01$) and C ($p=0.044$), and that AUC for meal LM was lower compared to meal WF ($p<0.01$)
Figure 2:
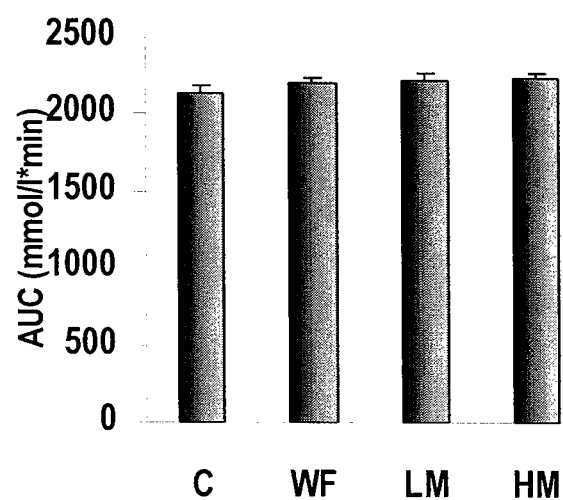
Figure 3:
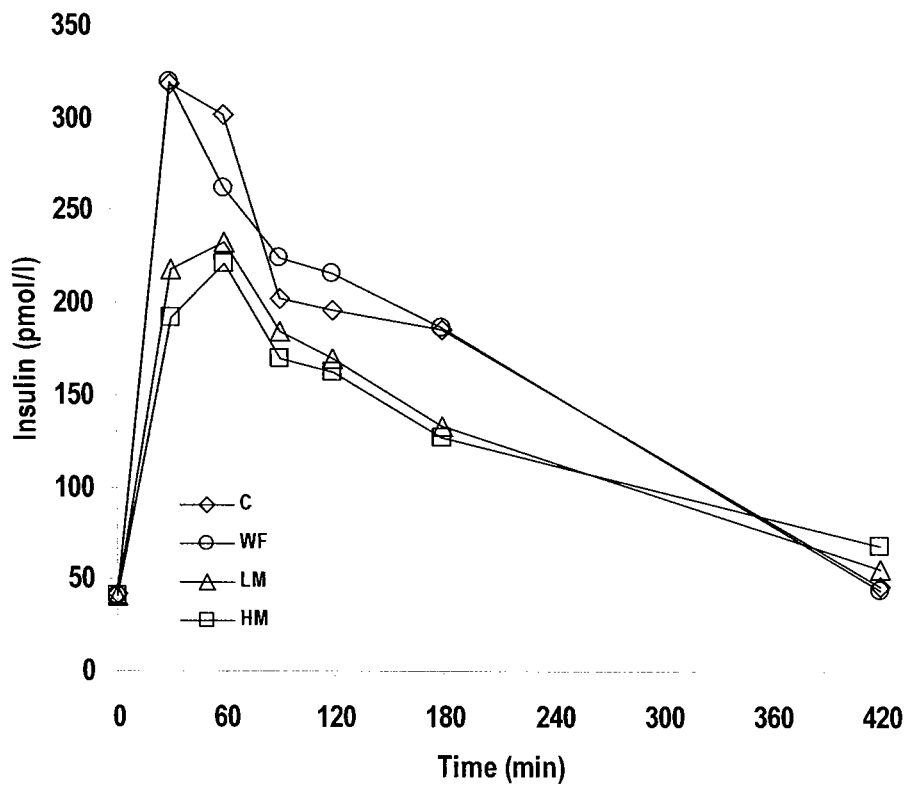
Figure 3:
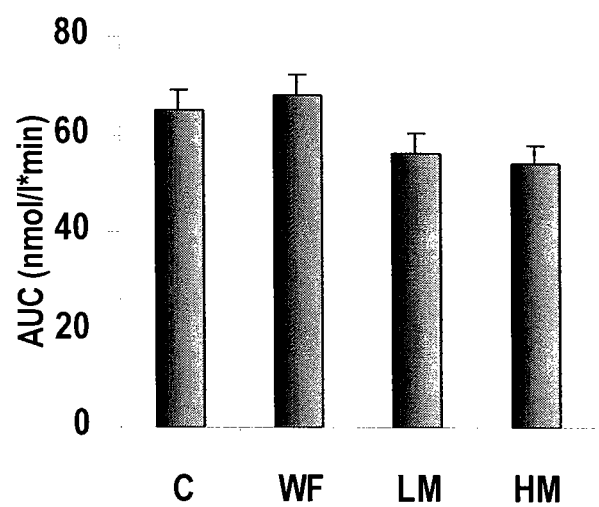
Figure 4:
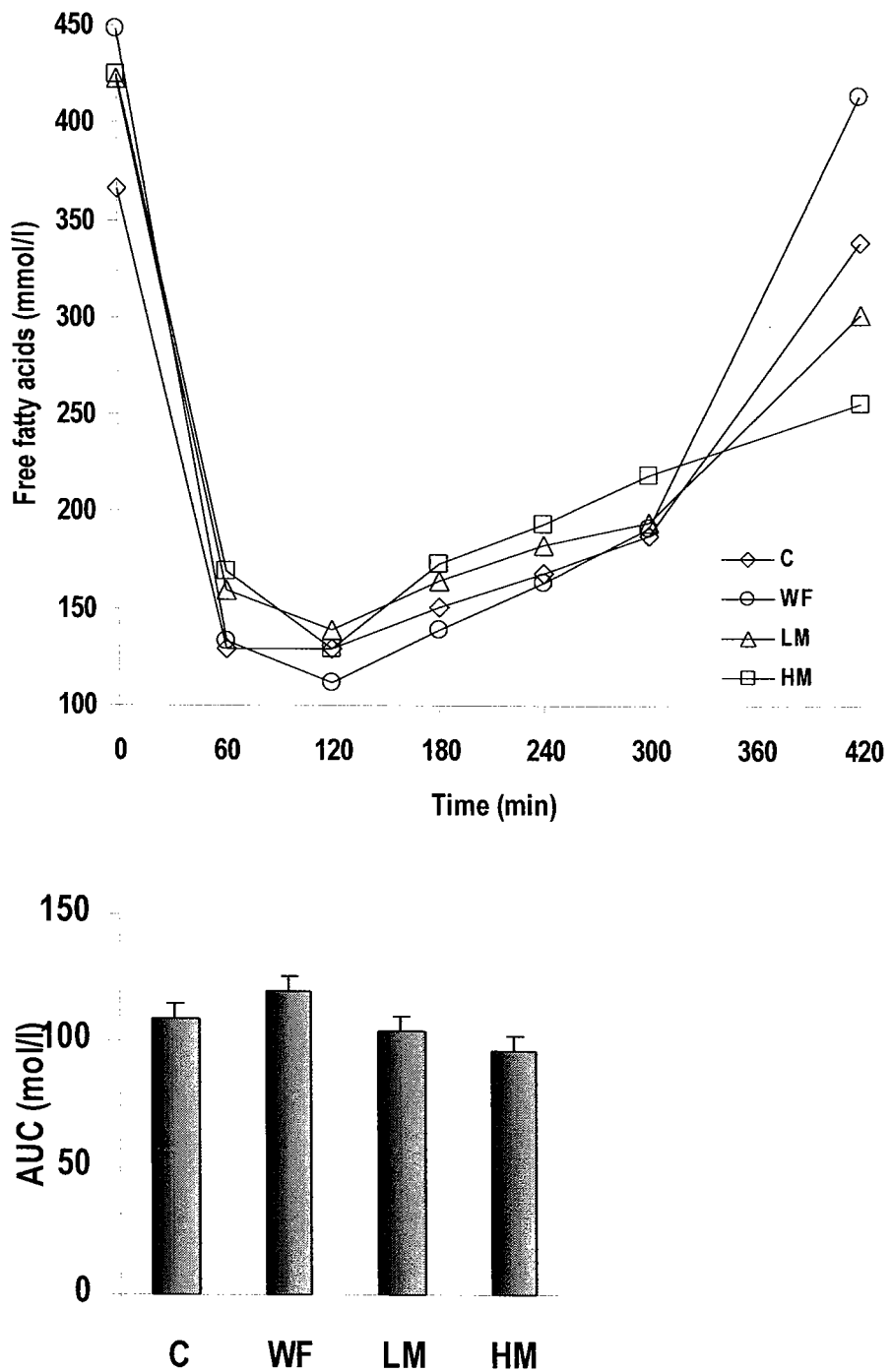

Repeated measures ANCOVA (adjusted for baseline, body weight and period) showed a strong effect of time on glucose, but no overall effect of meal. A strong time*meal interaction was observed for insulin ($p<0.01$). Posthoc pairwise comparisons that the HM meal resulted in lower insulin concentrations compared to meal WF and mean meal C after 30 minutes ($p<0.01$) and compared to meal WF at 180 minutes ($p=0.027$); and higher at 420 minutes compared to meal WF ($p<0.01$) and meal C ($p=0.027$). Meal LM gave lower insulin response compared to meal WF at 30 minutes ($p=0.026$). There was a drop in plasma glucose when described using the area under the curve (AUC) of app. 20% although non-significant ($p=0.19$) (FIG. 2). Interestingly, the whole flax seed do not exhibit the same effects on the glucose response as does the same dose (5 g fibre/meal) provided from flaxseed mucilage. There was however a significant effect on plasma insulin AUC ($p=0.012$) after adjustment for baseline levels (FIG. 3). Posthoc analyses using Tukey's adjustment showed significant differences between 10 g of fibre from flaxseed mucilage vs. 5 g of fibre from whole flaxseeds ($p=0.028$) and control ($p=0.034$) and differences between 10 g of fibre from flaxseed mucilage vs. control ($p<0.01$) and whole flaxseeds ($p<0.01$).

Figure 5:
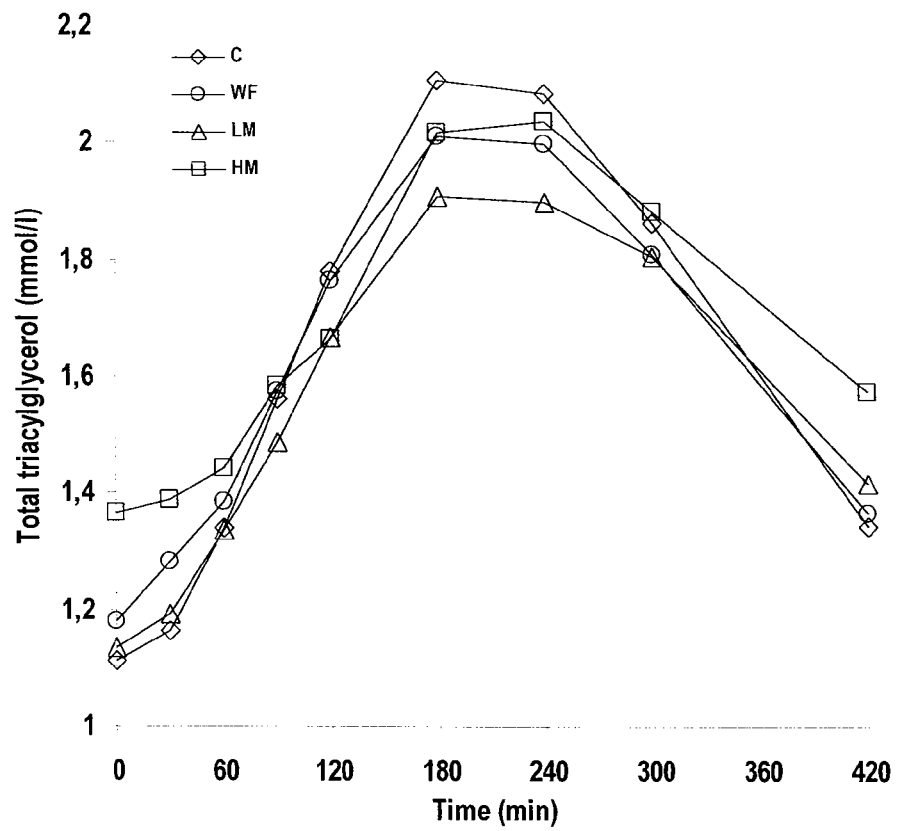
FIGS. 5-6 show unadjusted mean plasma triacylglycerol (TAG) (FIG. 5) and chylomicron TAG (FIG. 6) concentrations during the 7 hours after 4 iso-caloric test meals (C: control; WF: whole flaxseeds; LM: low dose flaxseed mucilage; HM: high dose flaxseed mucilage) and corresponding AUCs (least square means ±SEM) (n=17). Repeated-measures ANCOVA (adjusted for baseline, body weight and period) showed a strong effect of time on TAG ($p<0.001$), but no effect of meal on TAG ($p=0.164$), and a tendency towards a time*meal interaction for chylomicron TAG ($p=0.068$). ANCOVA (adjusted for baseline, body weight and period) showed an effect of meal on AUC for TAG ($p=0.016$, and posthoc comparisons revealed meal HM to give higher AUC for TAG than meal C ($p=0.009$). There was no effect of meal on AUC for chylomicron TAG ($p=0.321$)
Figure 5:
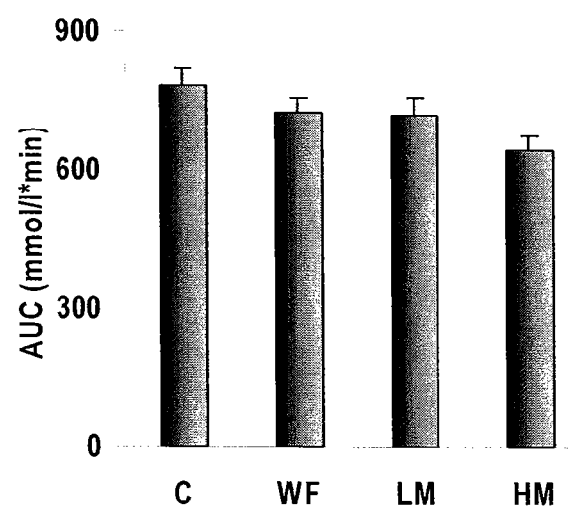
Figure 7:
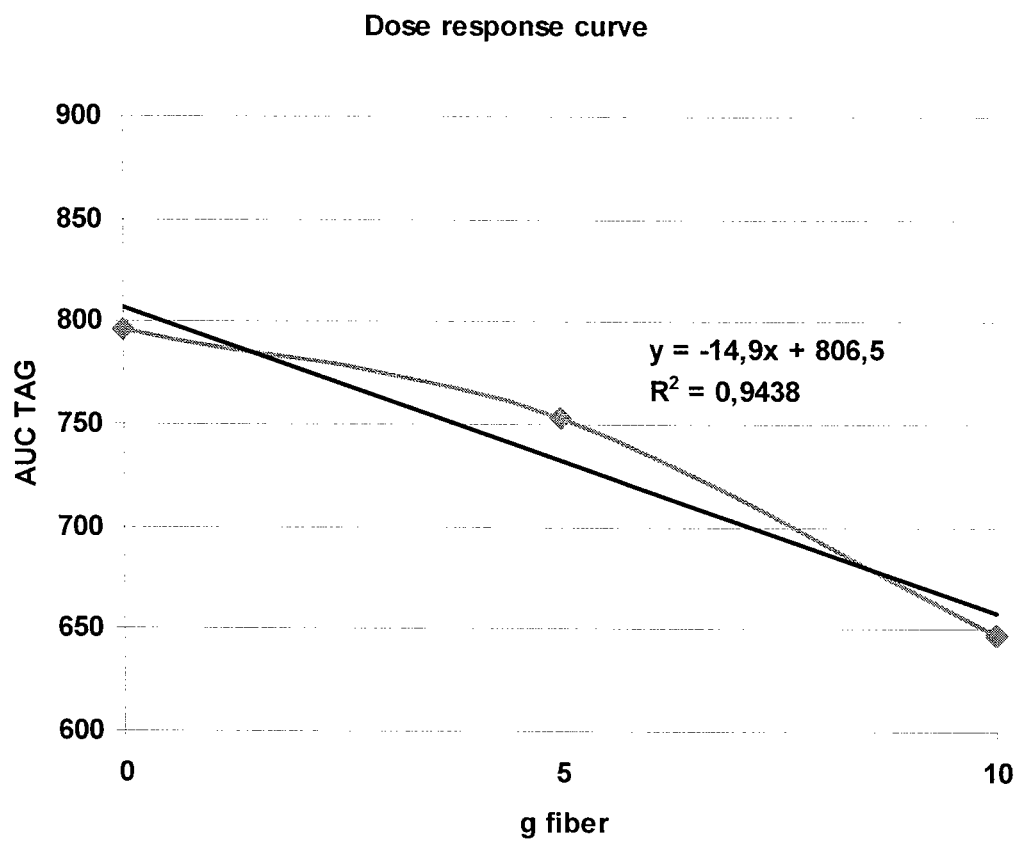
FIG. 7 shows the postprandial triacylglycerol response as a function of fiber content.
Figure 8:
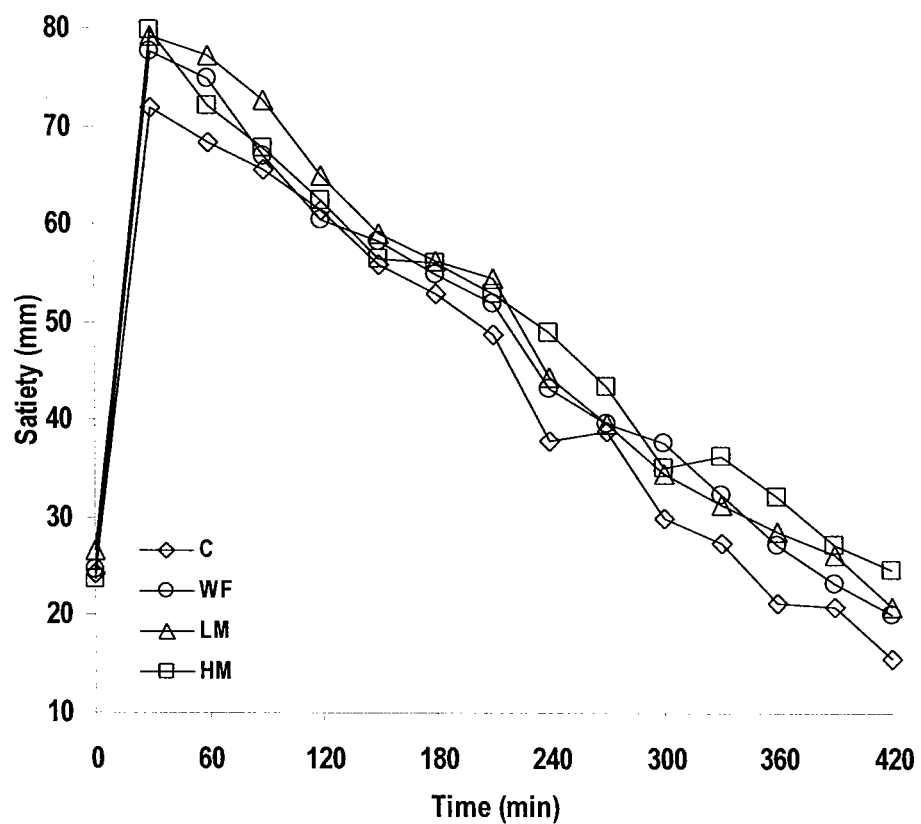
FIGS. 8-11 show unadjusted mean ratings of satiety (FIG. 8), fullness (FIG. 9), hunger (FIG. 10) and prospective consumption (FIG. 11) during the 7 hours after 4 iso-caloric test meals (C: control; WF: whole flaxseeds; LM: low dose flaxseed mucilage; HM: high dose flaxseed mucilage) and corresponding AUCs (least square means ±SEM) (n=18). Repeated-measures ANCOVA (adjusted for baseline, body weight and period) showed a strong effect of time on all measures (p<0.001), and an effect of meal on satiety (p=0.007), fullness (p=0.032), hunger (p=0.048) and prospective consumption (p=0.035). Posthoc pairwise comparisons showed that meal HM gave higher satiety and fullness ratings (p=0.008 and p=0.030, respectively) and lower hunger and prospective consumption ratings (p=0.040 and p=0.023, respectively). Meal LM gave higher satiety ratings compared to meal C (p=0.014). ANCOVA (adjusted for baseline, body weight and period) showed an effect of meal on AUC for satiety (p=0.009), fullness (p=0.025), hunger (p=0.033) and prospective consumption (p=0.026). Posthoc pairwise comparisons showed that AUC for satiety for meal LM and HM was larger than meal C (p=0.021 and p=0.008, respectively), that AUC for fullness for meal LM and HM was larger than meal C (p=0.050 and p=0.026, respectively). AUC for hunger and prospective consumption was lower for meal HM compared to meal C (p=0.028 and p=0.017, respectively)
Figure 8:
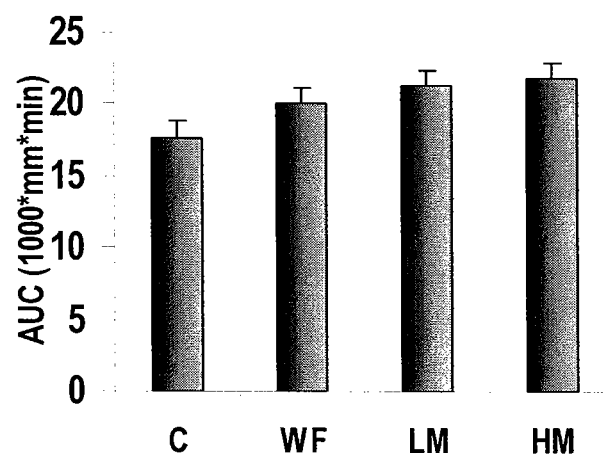
Figure 9:
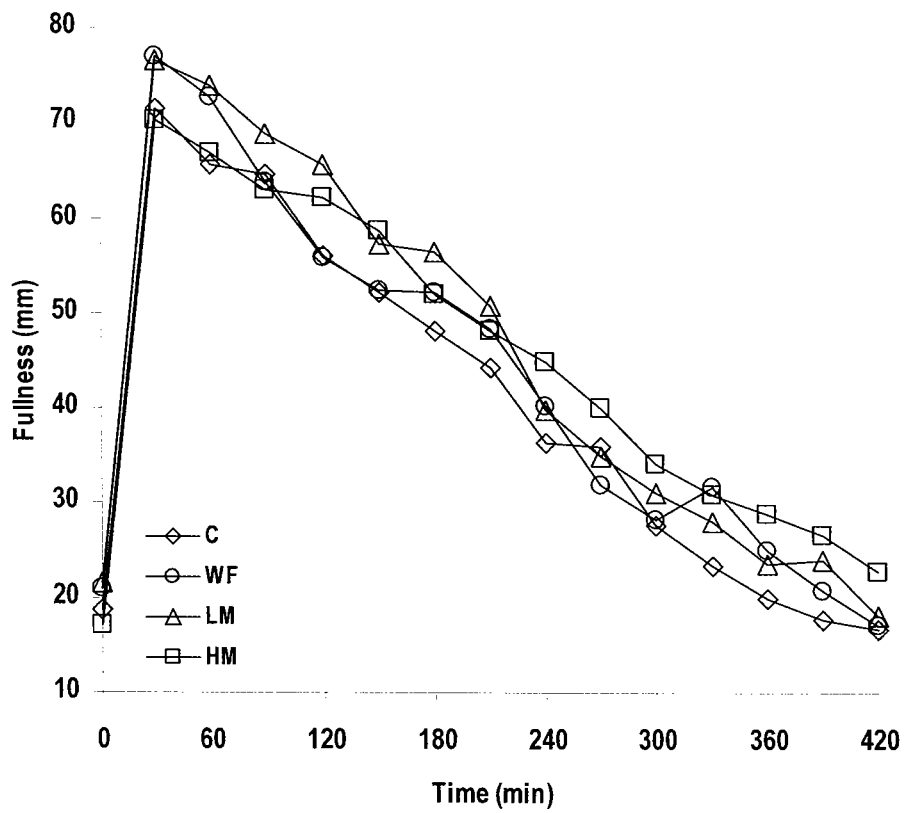
Figure 9:
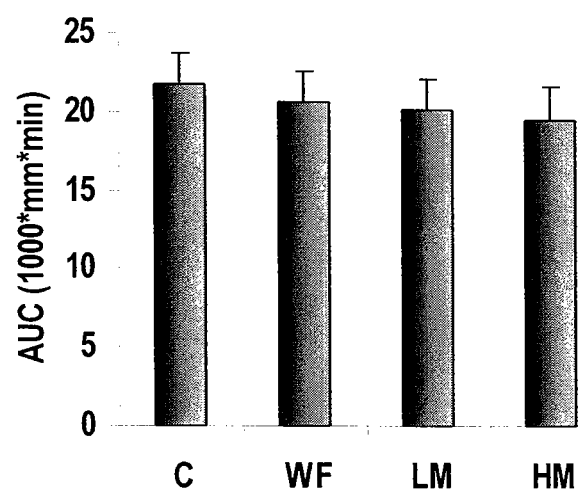
Figure 10:
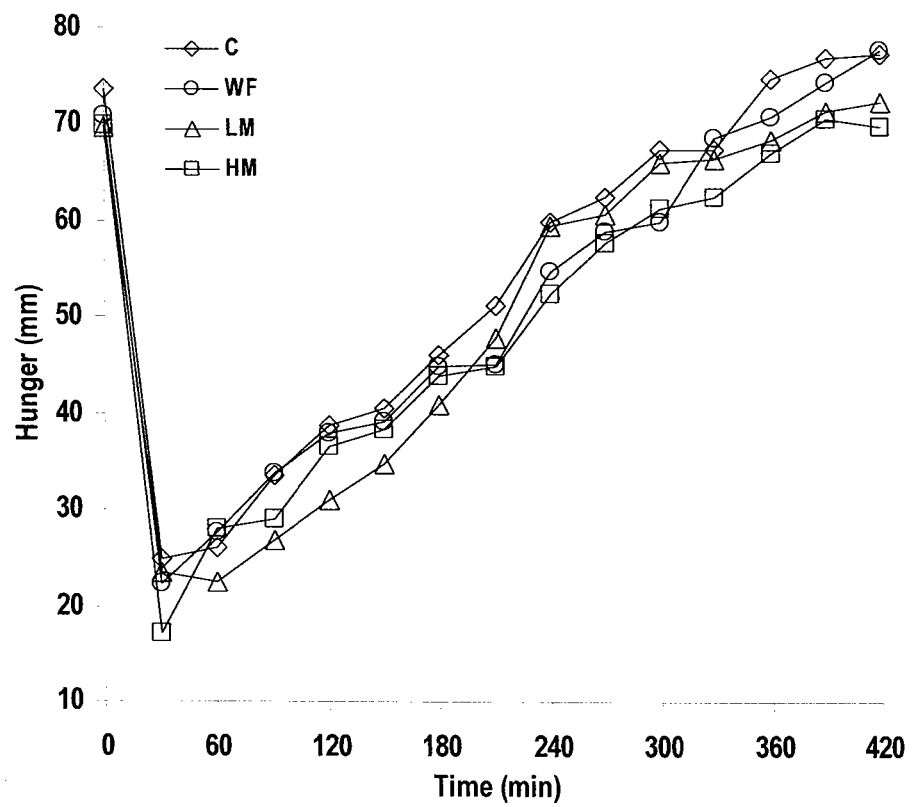
Figure 10:
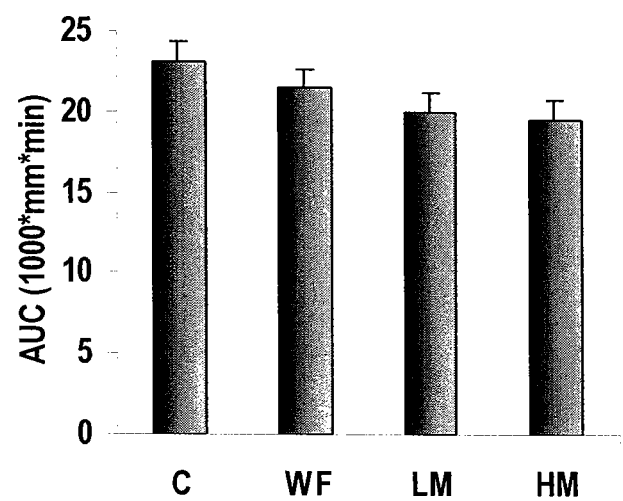
Figure 11:
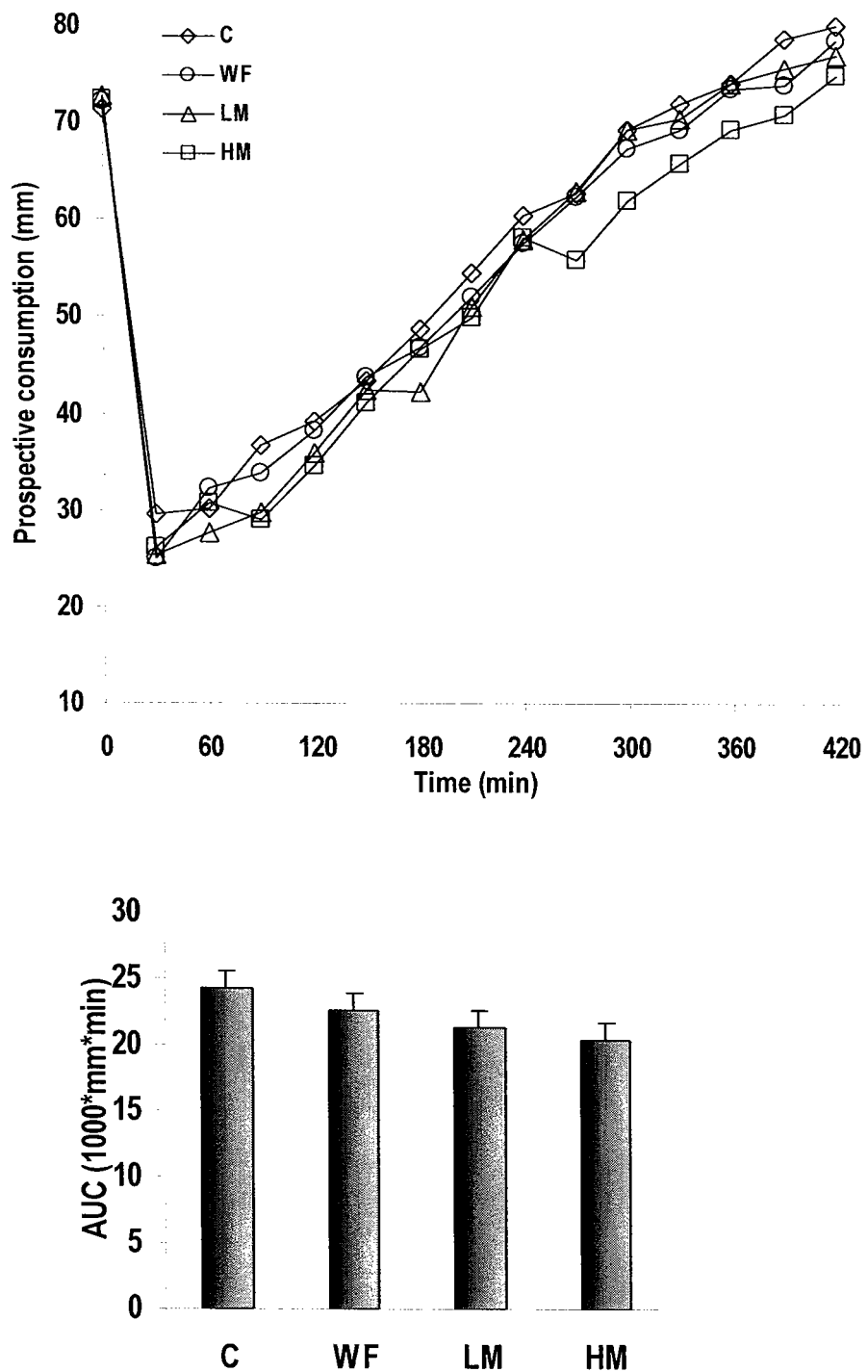

The acute response in total triacylglycerols (TAG) after the different test meals is shown in FIG. 5, where the control meal resulted in a larger increase in plasma TAG than the meal containing 10g of fibres from flaxseed mucilage. From the AUCs (FIG. 5) it is seen that there is an effect of treatment when adjusted for baseline levels of TAG ($p=0.016$), however, there are no significant differences between the control and the two meals providing 5 g of fibres from either whole flaxseed or flaxseed mucilage, whereas the high mucilage dose resulted in a significantly lower response compared to the control meal (−18%) ($p=0.009$). When considering only the control meal and the two meals containing 5 or 10 g of flaxseed mucilage, a dose-response relationship between the dose of fibre and TAG AUCs can be seen (FIG. 7), in which addition of 1 g of fibres as flaxseed mucilage corresponds to a drop in TAG AUC of 15 or app. 1.8%.

Figure 6:
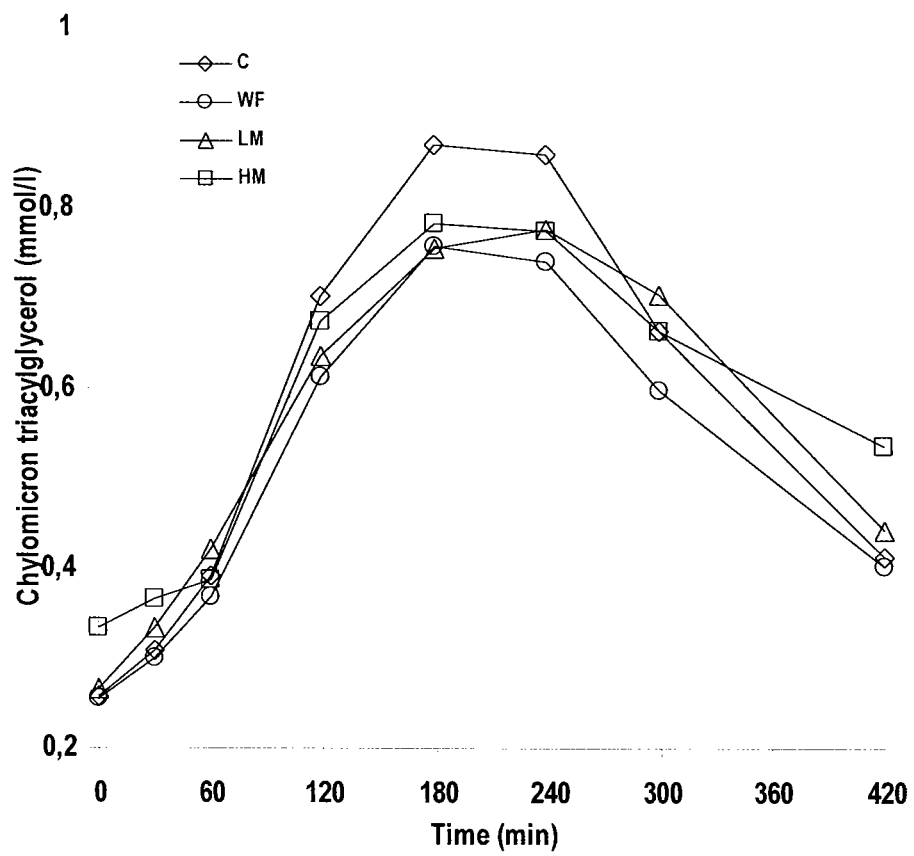
Figure 6:
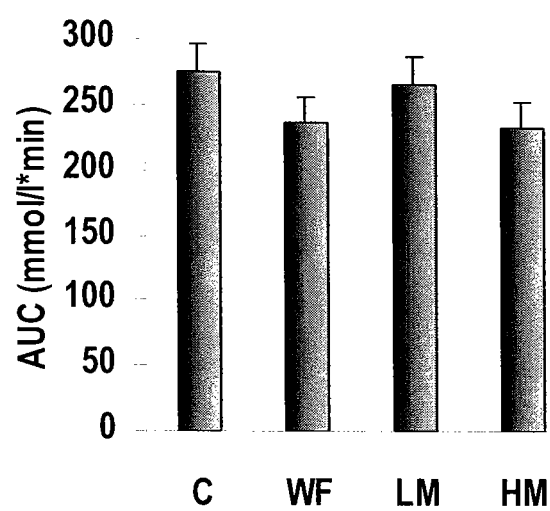

The postprandial chylomicron TAG response analyses showed a near-significant time*meal interaction (p=0.068), but there was no significant effect of meal on AUCs for chylomicron TAG (p=0.321) (FIG. 6).

There was also observed effects on subjective appetite sensation, in that the four parameters related to satiety (satiety, fullness, hunger and prospective food intake) were affected by diet. There was a significant overall effect of meal on satiety (p=0.007) and fullness (p=0.032) and compared with the C meal, the LM and HM meals resulted in significantly higher self-reported satiety (p=0.014 and p=0.008, respectively), and the HM meals resulted in increased fullness compared to meal C (p=0.030) after adjusting for baseline, body weight and period (FIGS. 8-11). Hunger sensation and prospective consumption were also significantly affected by meal (p=0.048 and p=0.035, respectively), meal HM resulting in significantly lower sensation of hunger and estimated prospective consumption than meal C (p=0.040 and p=0.023, respectively). An overall effect of meal on AUC for satiety was observed (p=0.009) and was 20 and 23% larger for LM and HM meals compared to meal C (p=0.021 and p=0.008, respectively), whereas no effect on AUC for fullness was observed. There was an overall meal effect on AUC for hunger (p=0.033) and prospective consumption (p=0.026), and they were lower for meal HM compared to meal C (p=0.028 and p=0.017, respectively).

Figure 12:
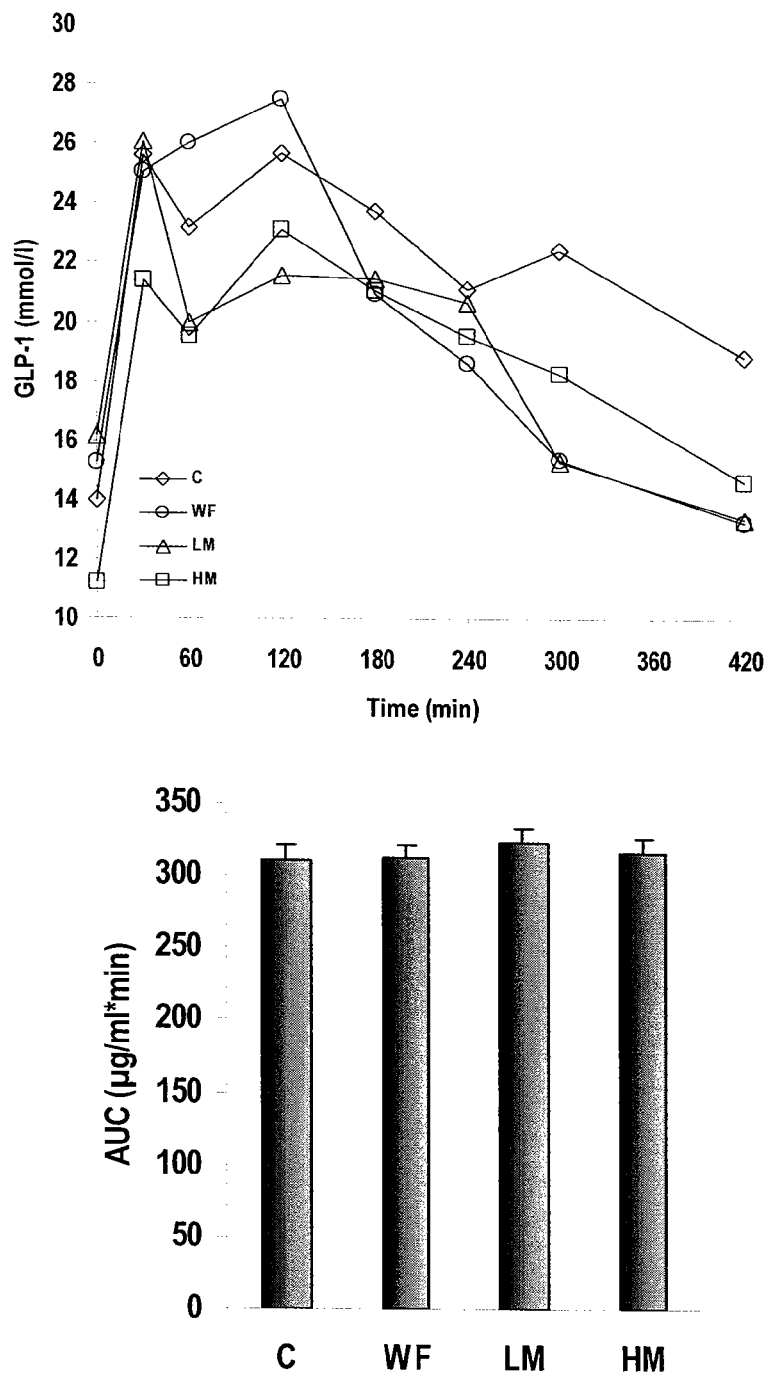
FIGS. 12-13 show unadjusted mean glucagon-like peptide-1 (GLP-1) (FIG. 12), and total ghrelin (FIG. 13) during the 7 hours after 4 iso-caloric test meals (C: control; WF: whole flaxseeds; LM: low dose flaxseed mucilage; HM: high dose flaxseed mucilage) and corresponding AUCs (least square means ±SEM) (n=18). Repeated measures ANCOVA (adjusted for baseline, body weight and period) showed a strong time*meal interaction for GLP-1 (p<0.01), CCK (p<0.01) and ghrelin (p<0.001). Posthoc pairwise comparisons showed GLP-1 to be larger for meal C a compared to meal WF and LM at 300 minutes (p=0.028 and p=0.034, respectively) and at 420 minutes (p=0.022 and p=0.032, respectively). Total ghrelin response after HM was lower at 420 minutes compared to C (p=0.012) and WF (p=0.009). ANCOVA (adjusted for baseline, body weight and period) showed no effect of meal on GLP-1 (p=0.315), CCK (p=0.306) or total ghrelin (p=0.40).
Figure 13:
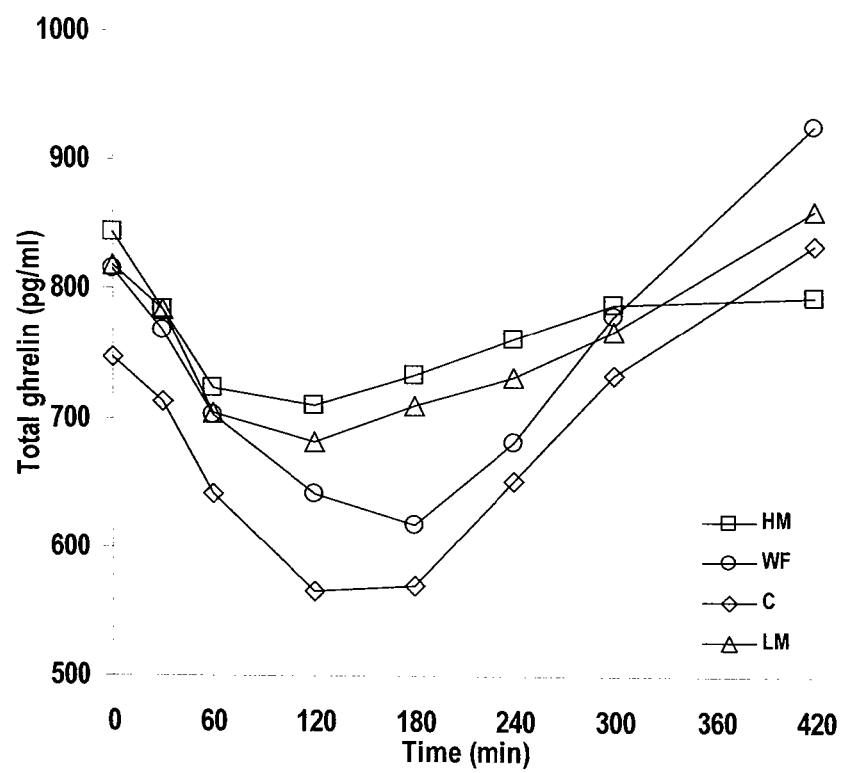
Figure 13:
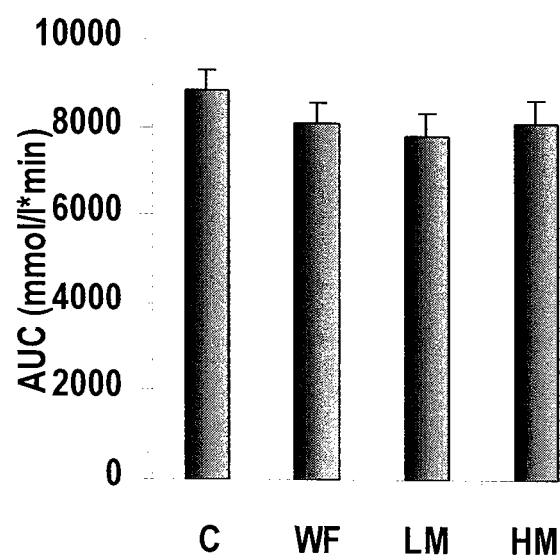

Repeated measures ANCOVA (adjusted for baseline, body weight and period) showed a strong time*meal interaction for GLP-1 (p<0.01) and ghrelin (p<0.001) (FIGS. 12-13). Posthoc pairwise comparisons showed GLP-1 to be larger for meal C a compared to meal WF and LM at 300 minutes (p=0.028 and p=0.034, respectively) and at 420 minutes (p=0.022 and p=0.032, respectively). Total ghrelin response after HM was lower at 420 minutes compared to C (p=0.012) and WF (p=0.009). ANCOVA (adjusted for baseline, body weight and period) showed no effect of meal on GLP-1 (p=0.315) or total ghrelin (p=0.040).

3.3 Discussion and Conclusion

The acute response of insulin is significantly reduced by the addition of 10 g of fibres from flaxseed mucilage to the test meal, although the reduction in glucose response did not reach statistical significance. Furthermore, there is a strong trend towards an increased effect of the mucilage compared to whole flaxseeds when given in comparable doses strongly indicating that the extracted mucilage fibres are more efficient than when the fibres are eaten in its normal matrix. Also, the same pattern is seen as with the glucose response, i.e. a lack of effect of whole flaxseeds compared to the same dose of fibres given as flaxseed mucilage, although not significant. The high dose used here represents only app. 35% of the recommended daily dose of fibres, thus if the dose is increased, the effect could be amplified and most likely the effects on glucose would reach statistical significance.

The response in plasma TAGs are used as a measure for lipid uptake, as dietary lipids reach the circulation as triacylglycerides and thus this measure is a strong indicator of how much of the lipids are absorbed. Thus, although fat excretion is not measured after these test meals, conclusions can be made on the lipid uptake based on these results. These results are also supported by the rat studies showing clear effects on fat digestibility. Furthermore, the postprandial TAG response represents a risk for cardiovascular disease in itself, thus reducing this response may affect cardiovascular risk.

Not only does the flaxseed mucilage decrease lipid uptake, but induce a noteworthy increase in the feeling of satiety and at the same time along with a decreased sensation of hunger and prospective food intake. The fact that these four measures related to the feeling of satiety were affected emphasizes the effectiveness of this food ingredient. There appeared to be a tendency towards a period effect on the four measures related to satiety, thus this factor is kept in the statistical model. The period effect can be explained by the seasonal change through the study (Dec to May) which may affect the subjects habitual food intake and thus also their sensation of appetite in response to a test meal. If this factor is removed from the model the effect of the test diets no longer persists.

Both GLP-1 and ghrelin are significantly different after the HM meal compared to the C meal at 420 min. Thus intermeal satiety persists 7 hours after intake of the test meal mediated by significantly increased GLP-1 levels at 420 min and hunger is suppressed after the HM meal as indicated by lower ghrelin levels at 420 min, which corresponds to the subjective ratings of both satiety and fullness and on the other hand hunger.

In conclusion, these results strongly suggest that flaxseed mucilage is an astoundingly potent agent affecting insulinaemia, lipaemia, and appetite sensation. The addition of flaxseed mucilage to foods affects which we have observed indicate that multiple aspects of the gastrointestinal (GI) function such as gastric emptying, prolonged and diminished nutrient absorption and increased bulking in the small intestine is affected. Thus, it represents a product which can be used to affect energy balance in terms of a decreased energy digestibility and reduced food intake through increased satiety, without presenting adverse effects, such as bloating or flatulence in the doses used here.

REFERENCES

Bansal S, Buring J E, Rifai N, Mora S, Sacks F M, Ridker P M., Fasting compared with nonfasting triglycerides and risk of cardiovascular events in women, JAMA. 2007 Jul. 18;298(3):336-8.

Bellisle F. Functional foods and the satiety cascade. Nutrition bulletin 2008; 3; 8-14.

Flint A, Raben A, Blundell J E, Astrup A. Reproducibility, power and validity of visual analogue scales in assessment of appetite sensations in single test meal studies. International Journal of Obesity 2000; 24 38-48.

The invention claimed is:

1. A method for inducing weight-loss in a subject in need thereof, said method comprising administering to said subject a composition comprising flaxseed mucilage and calcium.

2. The method according to claim 1, wherein the weight-loss is induced by increasing fecal fat excretion and/or enhancing fat binding ability of the mucilage in the subject.

3. The method according to claim 1, wherein said subject is a mammal.

4. The method according to claim 3, wherein the mammal is a human.

5. The method according to claim 3, wherein the mammal is overweight or obese.

6. The method according to claim 3, wherein the mammal is a non-human.

7. The method according to claim 1, wherein said calcium is derived from a dairy product.

8. The method according to claim 1, wherein said calcium is milk calcium.

9. The method according to claim 1, further comprising a lipase inhibitor.

10. The method according to claim 9, wherein said lipase inhibitor is orlistat, cetilistsat, or a pharmaceutically acceptable salt thereof.

11. The method according to claim 1, wherein the daily dose of flaxseed mucilage is 0.1 to 45 grams of mucilage/day.

12. The method according to claim 1, wherein the daily dose of flaxseed mucilage is 1 to 45 grams of mucilage/day.

13. The method according to claim 1, wherein the daily dose of flaxseed mucilage is 1 to 40 grams of mucilage/day.

14. The method according to claim 1, wherein the daily dose of flaxseed mucilage is 5 to 35 grams of mucilage/day.

15. The method according to claim 1, wherein said composition is a pharmaceutical composition, a feed, a food or beverage product, a food ingredient, a dietary supplement, or a combination thereof.

16. The method according to claim 15, wherein said composition is a dietary supplement.

17. The method according to claim 16, wherein said dietary supplement is in the form of a capsule, a pill, a tablet, a chewable tablet, a liquid, or a supplement bar.

18. The method according to claim 15, wherein said feed, food or beverage product, or dietary supplement is selected from the group consisting of a cereal, an energy bar, a snack food, a milk product, a baked product, a fruit product, a vegetable product, a meat product, a semi-manufactured product, a ready-to-eat meal, a beverage, and combinations thereof.

19. The method according to claim 15, wherein said feed, food and/or beverage product or dietary supplement is a pet food selected from the group consisting dog food, cat food, fish feed, bird feed, small animal feed and horse feed.

20. The method according to claim 15, wherein the total content of mucilage, when used as an ingredient or fortificant, in feed, food and/or beverage product correspond to a content of 1 to 50% of mucilage by weight of the feed, food and/or beverage product.

21. The method according to claim 15, wherein the total content of mucilage, when used as an ingredient or fortificant, in feed, food and/or beverage product correspond to a content of 5 to 40% of mucilage by weight of the feed, food and/or beverage product.

22. The method according to claim 15, wherein the total content of mucilage, when used as an ingredient or fortificant, in feed, food and/or beverage product correspond to a content of 10 to 30% of mucilage by weight of the feed, food and/or beverage product.

23. The method according to claim 15, wherein the total content of mucilage, when used as an ingredient or fortificant, in feed, food and/or beverage product correspond to a content of 15 to 25% of mucilage by weight of the feed, food and/or beverage product.

24. The method according to claim 15, wherein the total content of mucilage, when used as a dietary supplement or food ingredient, corresponds to up to 90% by weight of said food ingredient or dietary supplement.

25. The method according to claim 15, wherein the total content of mucilage, when used as a dietary supplement or food ingredient is 50 to 75% by weight of said food ingredient or dietary supplement.

* * * * *